US011931165B2

(12) United States Patent
Askem et al.

(10) Patent No.: US 11,931,165 B2
(45) Date of Patent: Mar. 19, 2024

(54) ELECTROSTATIC DISCHARGE PROTECTION FOR SENSORS IN WOUND THERAPY

(71) Applicant: Smith & Nephew PLC, Watford (GB)

(72) Inventors: Ben Alan Askem, Leeds (GB); Fernando Bettani, Milan (IT); Alberto Fasan, Milan (IT); Allan Kenneth Frazer Grugeon Hunt, Beverely (GB); Felix Clarence Quintanar, Hull (GB); Daniel Lee Steward, Hull (GB)

(73) Assignee: Smith & Nephew PLC, Watford (GB)

( * ) Notice: Subject to any disclaimer, the term of this patent is extended or adjusted under 35 U.S.C. 154(b) by 605 days.

(21) Appl. No.: 16/641,960

(22) PCT Filed: Sep. 7, 2018

(86) PCT No.: PCT/EP2018/074180
§ 371 (c)(1),
(2) Date: Feb. 25, 2020

(87) PCT Pub. No.: WO2019/048626
PCT Pub. Date: Mar. 14, 2019

(65) Prior Publication Data
US 2020/0222597 A1 Jul. 16, 2020

Related U.S. Application Data

(60) Provisional application No. 62/556,450, filed on Sep. 10, 2017.

(30) Foreign Application Priority Data

Mar. 28, 2018 (GB) ...................... 1804971

(51) Int. Cl.
A61B 5/00 (2006.01)
A61M 1/00 (2006.01)
H05K 1/02 (2006.01)

(52) U.S. Cl.
CPC ............... *A61B 5/445* (2013.01); *A61M 1/73* (2021.05); *A61M 1/915* (2021.05); *A61M 1/95* (2021.05);
(Continued)

(58) Field of Classification Search
CPC .. A61M 1/73; A61M 1/90; A61M 2205/3306; A61M 2205/3317;
(Continued)

(56) References Cited

U.S. PATENT DOCUMENTS 3,896,802 A 7/1975 Williams
4,334,530 A 6/1982 Hassell
(Continued)

FOREIGN PATENT DOCUMENTS

CN 105232229 A 1/2016
CN 105395184 A 3/2016
(Continued)

OTHER PUBLICATIONS

Willis B., "Guide to Conformal Coating & Cleaning Defects Contents," Mar. 1, 2014, retrieved from http://coatingguide.smartgroup.org/ Files%20pdf/Coating%20Defects%20V2%201 Mar. 4, 2014 .pdf, vol. 1, 31 pages (Year: 2014).*
(Continued)

Primary Examiner — Andrew J Mensh
(74) Attorney, Agent, or Firm — Knobbe, Martens, Olson & Bear, LLP

(57) ABSTRACT

An apparatus for use in monitoring or treating a wound is disclosed. The apparatus can include a wound dressing, a circuit board, and a sensor. The wound dressing can be
(Continued)

positioned over a wound of a patient and absorb wound exudate from the wound. The circuit board can be incorporated in or coupled to the wound dressing and include a first conductive pathway extending around at least part of a perimeter of a first side of the circuit board. The first conductive pathway can be electrically coupled to an electrical ground for the circuit board. The sensor can be mounted on the circuit board and output a signal usable to determine a value indicative of a physiological parameter of the patient. The first conductive pathway can protect the sensor against an electrostatic discharge.

19 Claims, 15 Drawing Sheets

(52) U.S. Cl.
CPC .......... *H05K 1/0215* (2013.01); *H05K 1/0259* (2013.01); *A61M 1/985* (2021.05); *A61M 2205/3306* (2013.01); *A61M 2205/3317* (2013.01); *A61M 2205/3368* (2013.01); *H05K 2201/10151* (2013.01)

(58) Field of Classification Search
CPC ........... A61M 2205/3368; A61B 5/445; H05K 1/0215; H05K 1/0259; H05K 2201/10151
USPC .......................................................... 604/543
See application file for complete search history.

(56) References Cited

U.S. PATENT DOCUMENTS

| | | |
|---|---|---|
| 4,456,800 A | 6/1984 | Holland |
| 5,090,410 A | 2/1992 | Saper et al. |
| 5,253,654 A | 10/1993 | Thomas et al. |
| 5,635,201 A | 6/1997 | Fabo |
| 5,642,096 A | 6/1997 | Leyerer et al. |
| 5,678,448 A | 10/1997 | Fullen et al. |
| 5,690,610 A | 11/1997 | Ito et al. |
| 5,836,990 A | 11/1998 | Li |
| 6,095,992 A | 8/2000 | Augustine |
| 6,178,342 B1 | 1/2001 | Borgos et al. |
| 6,381,482 B1 | 4/2002 | Jayaraman et al. |
| 6,493,198 B1 | 12/2002 | Arledge et al. |
| 6,517,484 B1 | 2/2003 | Wilk et al. |
| 6,551,252 B2 | 4/2003 | Sackner et al. |
| 6,731,987 B1 | 5/2004 | McAdams et al. |
| 7,077,832 B2 | 7/2006 | Fleischmann |
| 7,201,063 B2 | 4/2007 | Taylor |
| 7,206,623 B2 | 4/2007 | Blank et al. |
| 7,289,205 B2 | 10/2007 | Yaroslavsky et al. |
| 7,316,652 B2 | 1/2008 | Dalgaard et al. |
| 7,429,255 B2 | 9/2008 | Thompson |
| 7,520,875 B2 | 4/2009 | Bernabei |
| 7,521,292 B2 | 4/2009 | Rogers et al. |
| 7,557,302 B2 | 7/2009 | Wang |
| 7,569,742 B2 | 8/2009 | Haggstrom et al. |
| 7,625,117 B2 | 12/2009 | Haslett et al. |
| 7,687,678 B2 | 3/2010 | Jacobs |
| 7,846,141 B2 | 12/2010 | Weston |
| 7,877,866 B1 | 2/2011 | Greenberg et al. |
| 7,884,258 B2 | 2/2011 | Boehringer et al. |
| 7,904,133 B2 | 3/2011 | Gehman et al. |
| 7,922,676 B2 | 4/2011 | Daskal et al. |
| 7,942,869 B2 | 5/2011 | Houbolt et al. |
| 7,945,302 B2 | 5/2011 | Mcadams |
| 8,019,401 B1 | 9/2011 | Smith et al. |
| 8,032,210 B2 | 10/2011 | Finneran et al. |
| 8,060,174 B2 | 11/2011 | Simpson et al. |
| 8,079,247 B2 | 12/2011 | Russell et al. |
| 8,111,165 B2 | 2/2012 | Ortega et al. |
| 8,116,841 B2 | 2/2012 | Bly et al. |
| 8,182,425 B2 | 5/2012 | Stamatas et al. |
| 8,238,996 B2 | 8/2012 | Burnes et al. |
| 8,241,231 B2 | 8/2012 | Bausewein et al. |
| 8,332,053 B1 | 12/2012 | Patterson et al. |
| 8,333,874 B2 | 12/2012 | Currie |
| 8,480,641 B2 | 7/2013 | Jacobs |
| 8,579,872 B2 | 11/2013 | Coulthard et al. |
| 8,644,911 B1 | 2/2014 | Panasyuk et al. |
| 8,663,106 B2 | 3/2014 | Stivoric et al. |
| 8,682,442 B2 | 3/2014 | Mcadams |
| 8,783,948 B2 | 7/2014 | Panda et al. |
| 8,788,009 B2 | 7/2014 | Greene et al. |
| 8,800,386 B2 | 8/2014 | Taylor |
| 8,818,478 B2 | 8/2014 | Scheffler et al. |
| 8,848,187 B2 | 9/2014 | Uematsu et al. |
| 8,894,590 B2 | 11/2014 | Lamoise et al. |
| 8,925,392 B2 | 1/2015 | Esposito et al. |
| 8,934,957 B2 | 1/2015 | Dias et al. |
| 8,934,965 B2 | 1/2015 | Rogers et al. |
| 8,943,897 B2 | 2/2015 | Beauvais et al. |
| 8,948,839 B1 | 2/2015 | Longinotti-Buitoni et al. |
| 8,997,588 B2 | 4/2015 | Taylor |
| 9,000,251 B2 | 4/2015 | Murphy et al. |
| 9,042,075 B2 | 5/2015 | Borini et al. |
| 9,192,531 B2 | 11/2015 | Wu |
| 9,220,455 B2 | 12/2015 | Sarrafzadeh et al. |
| 9,226,402 B2 | 12/2015 | Hsu |
| 9,282,897 B2 | 3/2016 | Ross et al. |
| 9,314,175 B2 | 4/2016 | Jacofsky et al. |
| 9,320,473 B2 | 4/2016 | Shuler |
| 9,372,123 B2 | 6/2016 | Li et al. |
| 9,378,450 B1 | 6/2016 | Mei et al. |
| 9,386,947 B2 | 7/2016 | Johnson |
| 9,393,354 B2 | 7/2016 | Freedman et al. |
| 9,402,988 B2 | 8/2016 | Buchanan et al. |
| 9,408,573 B2 | 8/2016 | Welch et al. |
| 9,427,179 B2 | 8/2016 | Mestrovic et al. |
| 9,439,599 B2 | 9/2016 | Thompson et al. |
| 9,483,726 B2 | 11/2016 | Mei et al. |
| 9,494,474 B2 | 11/2016 | Servati et al. |
| 9,511,215 B2 | 12/2016 | Skiba |
| 9,516,758 B2 | 12/2016 | Arora et al. |
| 9,526,439 B2 | 12/2016 | Connelly et al. |
| 9,554,484 B2 | 1/2017 | Rogers et al. |
| 9,572,507 B2 | 2/2017 | Moore et al. |
| 9,582,072 B2 | 2/2017 | Connor |
| 9,585,620 B2 | 3/2017 | Paquet et al. |
| 9,587,991 B2 | 3/2017 | Padiy |
| 9,592,007 B2 | 3/2017 | Nuovo et al. |
| 9,603,560 B2 | 3/2017 | Monty et al. |
| 9,610,388 B2 | 4/2017 | Aceto et al. |
| 9,613,911 B2 | 4/2017 | Rogers et al. |
| 9,629,584 B2 | 4/2017 | Macia Barber et al. |
| 9,675,238 B2 | 6/2017 | Iida et al. |
| 9,687,195 B2 | 6/2017 | Sims et al. |
| 9,717,565 B2 | 8/2017 | Blair |
| 9,829,471 B2 | 11/2017 | Hammond et al. |
| 9,907,103 B2 | 2/2018 | Chen et al. |
| 10,004,643 B2 | 6/2018 | Luckemeyer et al. |
| 10,046,096 B2 | 8/2018 | Askem et al. |
| 10,076,449 B2 | 9/2018 | Allen et al. |
| 10,080,524 B1 | 9/2018 | Xi |
| 10,117,705 B2 | 11/2018 | Chernov et al. |
| 10,152,789 B2 | 12/2018 | Carnes et al. |
| 10,182,740 B2 | 1/2019 | Tonar et al. |
| 10,207,031 B2 | 2/2019 | Toth |
| 10,209,213 B2 | 2/2019 | Kang et al. |
| 10,285,620 B2 | 5/2019 | Jung et al. |
| 10,321,862 B2 | 6/2019 | Dalene et al. |
| 10,463,773 B2 | 11/2019 | Haggstrom et al. |
| 10,857,038 B2 | 12/2020 | Zamierowski et al. |
| 11,026,847 B2 | 6/2021 | Piotrowski et al. |
| 11,647,922 B2 | 5/2023 | Scherer |
| 2002/0016536 A1 | 2/2002 | Benni |
| 2002/0135752 A1 | 9/2002 | Sokolov et al. |
| 2003/0033032 A1 | 2/2003 | Lind et al. |
| 2003/0208148 A1 | 11/2003 | Sullivan |
| 2003/0210810 A1 | 11/2003 | Gee, Jr. et al. |
| 2003/0216630 A1 | 11/2003 | Jersey-Willuhn et al. |
| 2004/0230132 A1 | 11/2004 | Shehada |

(56) References Cited

U.S. PATENT DOCUMENTS

| | | |
|---|---|---|
| 2005/0088832 A1 | 4/2005 | Su et al. |
| 2005/0240107 A1 | 10/2005 | Alfano et al. |
| 2005/0280531 A1 | 12/2005 | Fadem et al. |
| 2006/0052678 A1 | 3/2006 | Drinan et al. |
| 2006/0058690 A1 | 3/2006 | Bartnik et al. |
| 2006/0181791 A1 | 8/2006 | Van Beek et al. |
| 2006/0234383 A1 | 10/2006 | Gough |
| 2006/0241495 A1 | 10/2006 | Kurtz |
| 2007/0055209 A1 | 3/2007 | Patel et al. |
| 2007/0173892 A1 | 7/2007 | Fleischer et al. |
| 2007/0191754 A1 | 8/2007 | Aali |
| 2007/0260421 A1 | 11/2007 | Berner et al. |
| 2007/0293748 A1 | 12/2007 | Engvall et al. |
| 2008/0081973 A1 | 4/2008 | Hoarau |
| 2008/0167535 A1 | 7/2008 | Stivoric et al. |
| 2008/0258717 A1 | 10/2008 | Igney et al. |
| 2008/0275409 A1 | 11/2008 | Kane et al. |
| 2008/0287747 A1 | 11/2008 | Mestrovic et al. |
| 2008/0319282 A1 | 12/2008 | Tran |
| 2008/0319283 A1 | 12/2008 | Cotton et al. |
| 2009/0149800 A1 | 6/2009 | Durand |
| 2009/0177051 A1 | 7/2009 | Arons et al. |
| 2009/0177110 A1 | 7/2009 | Lyden et al. |
| 2009/0209830 A1 | 8/2009 | Nagle et al. |
| 2009/0234206 A1 | 9/2009 | Gaspard et al. |
| 2009/0245601 A1 | 10/2009 | Cohen et al. |
| 2010/0022990 A1 | 1/2010 | Karpowicz et al. |
| 2010/0025831 A1 | 2/2010 | Yamazaki et al. |
| 2010/0166252 A1 | 7/2010 | Ahmed et al. |
| 2010/0168727 A1 | 7/2010 | Hancock et al. |
| 2010/0305473 A1 | 12/2010 | Yuzhakov |
| 2011/0004088 A1 | 1/2011 | Grossman |
| 2011/0015591 A1 | 1/2011 | Hanson et al. |
| 2011/0054283 A1 | 3/2011 | Shuler |
| 2011/0130697 A1 | 6/2011 | Nagle et al. |
| 2011/0140703 A1 | 6/2011 | Chiao et al. |
| 2011/0190639 A1 | 8/2011 | Peltie et al. |
| 2011/0218757 A1 | 9/2011 | Callsen et al. |
| 2011/0242532 A1 | 10/2011 | Mckenna |
| 2011/0245682 A1 | 10/2011 | Robinson et al. |
| 2011/0301441 A1 | 12/2011 | Bandic et al. |
| 2012/0029306 A1 | 2/2012 | Paquet et al. |
| 2012/0029307 A1 | 2/2012 | Paquet et al. |
| 2012/0029410 A1 | 2/2012 | Koenig et al. |
| 2012/0112347 A1 | 5/2012 | Eckhardt et al. |
| 2012/0165717 A1 | 6/2012 | Al Khaburi |
| 2012/0190956 A1 | 7/2012 | Connolly |
| 2012/0190989 A1 | 7/2012 | Kaiser et al. |
| 2012/0265120 A1 | 10/2012 | Beisang, III et al. |
| 2012/0271265 A1 | 10/2012 | Langdon |
| 2012/0277559 A1 | 11/2012 | Kohl-Bareis et al. |
| 2012/0316538 A1 | 12/2012 | Heiser et al. |
| 2012/0323098 A1 | 12/2012 | Moein et al. |
| 2012/0330252 A1 | 12/2012 | Stokes et al. |
| 2013/0041235 A1 | 2/2013 | Rogers et al. |
| 2013/0064772 A1 | 3/2013 | Swiss et al. |
| 2013/0121544 A1 | 5/2013 | Sarrafzadeh et al. |
| 2013/0123722 A1 | 5/2013 | Pratt et al. |
| 2013/0151223 A1 | 6/2013 | Zamierowski et al. |
| 2013/0200268 A1 | 8/2013 | Rafferty et al. |
| 2013/0261409 A1 | 10/2013 | Pathak et al. |
| 2013/0271278 A1 | 10/2013 | Duesterhoft et al. |
| 2013/0274563 A1* | 10/2013 | Duesterhoft ......... A61B 5/6885 600/300 |
| 2013/0274629 A1 | 10/2013 | Duesterhoft et al. |
| 2013/0317367 A1 | 11/2013 | Shuler |
| 2014/0005618 A1 | 1/2014 | Locke et al. |
| 2014/0012108 A1 | 1/2014 | Mcpeak |
| 2014/0018637 A1 | 1/2014 | Bennett et al. |
| 2014/0024905 A1 | 1/2014 | Sarrafzadeh et al. |
| 2014/0031663 A1 | 1/2014 | Gallego et al. |
| 2014/0072190 A1 | 3/2014 | Wu et al. |
| 2014/0075658 A1 | 3/2014 | Mcguin |
| 2014/0107495 A1 | 4/2014 | Marinelli et al. |
| 2014/0107498 A1 | 4/2014 | Bower et al. |
| 2014/0147611 A1 | 5/2014 | Ackerman, Jr. |
| 2014/0203797 A1 | 7/2014 | Stivoric et al. |
| 2014/0206947 A1 | 7/2014 | Isserow et al. |
| 2014/0232516 A1 | 8/2014 | Stivoric et al. |
| 2014/0235166 A1 | 8/2014 | Molettiere et al. |
| 2014/0243709 A1 | 8/2014 | Gibson et al. |
| 2014/0296749 A1 | 10/2014 | Reid, Jr. et al. |
| 2014/0298927 A1 | 10/2014 | Allin et al. |
| 2014/0298928 A1 | 10/2014 | Duesterhoft et al. |
| 2014/0303463 A1 | 10/2014 | Robinson et al. |
| 2014/0324120 A1 | 10/2014 | Bogie et al. |
| 2014/0340857 A1 | 11/2014 | Hsu et al. |
| 2014/0343478 A1 | 11/2014 | Brennan et al. |
| 2014/0343518 A1 | 11/2014 | Riesinger |
| 2014/0350882 A1 | 11/2014 | Everett et al. |
| 2015/0018792 A1 | 1/2015 | Marsiquet et al. |
| 2015/0025343 A1 | 1/2015 | Gareau et al. |
| 2015/0138330 A1 | 5/2015 | Krishnamoorthi |
| 2015/0141767 A1 | 5/2015 | Rogers et al. |
| 2015/0148760 A1 | 5/2015 | Dodd et al. |
| 2015/0150479 A1 | 6/2015 | Yoshino et al. |
| 2015/0182166 A1 | 7/2015 | Evans et al. |
| 2015/0223716 A1 | 8/2015 | Korkala et al. |
| 2015/0257644 A1 | 9/2015 | Cao |
| 2015/0265191 A1 | 9/2015 | Harding et al. |
| 2015/0292968 A1 | 10/2015 | Vogt et al. |
| 2015/0313476 A1 | 11/2015 | Pisani et al. |
| 2015/0313533 A1 | 11/2015 | Rapp et al. |
| 2015/0327777 A1 | 11/2015 | Kostic et al. |
| 2015/0335254 A1 | 11/2015 | Fastert et al. |
| 2015/0335287 A1 | 11/2015 | Neuman et al. |
| 2015/0335288 A1 | 11/2015 | Toth et al. |
| 2015/0351970 A1 | 12/2015 | Dagger et al. |
| 2015/0359485 A1 | 12/2015 | Berg et al. |
| 2015/0374309 A1 | 12/2015 | Farkas et al. |
| 2016/0015962 A1 | 1/2016 | Shokoueinejad et al. |
| 2016/0022223 A1 | 1/2016 | Grundfest et al. |
| 2016/0029900 A1 | 2/2016 | Laplante et al. |
| 2016/0030132 A1 | 2/2016 | Cheung et al. |
| 2016/0038045 A1 | 2/2016 | Shapiro |
| 2016/0038083 A1 | 2/2016 | Ding et al. |
| 2016/0051147 A1 | 2/2016 | Cohen et al. |
| 2016/0058380 A1 | 3/2016 | Lee et al. |
| 2016/0066854 A1 | 3/2016 | Mei et al. |
| 2016/0069743 A1 | 3/2016 | Mcquilkin et al. |
| 2016/0074234 A1 | 3/2016 | Abichandani et al. |
| 2016/0081580 A1 | 3/2016 | Bergelin et al. |
| 2016/0081601 A1 | 3/2016 | Ballam et al. |
| 2016/0100790 A1 | 4/2016 | Cantu et al. |
| 2016/0100987 A1 | 4/2016 | Hartwell et al. |
| 2016/0101282 A1 | 4/2016 | Bergelin et al. |
| 2016/0129469 A1 | 5/2016 | Kulinsky et al. |
| 2016/0143534 A1 | 5/2016 | Hyde et al. |
| 2016/0157779 A1 | 6/2016 | Baxi et al. |
| 2016/0165719 A1 | 6/2016 | Li et al. |
| 2016/0166438 A1 | 6/2016 | Rovaniemi |
| 2016/0213269 A1 | 7/2016 | Lam et al. |
| 2016/0228049 A1 | 8/2016 | Nackaerts et al. |
| 2016/0232807 A1 | 8/2016 | Ghaffari et al. |
| 2016/0249810 A1 | 9/2016 | Darty et al. |
| 2016/0262672 A1 | 9/2016 | Hammond et al. |
| 2016/0262687 A1 | 9/2016 | Vaidyanathan et al. |
| 2016/0270700 A1 | 9/2016 | Baxi et al. |
| 2016/0287177 A1 | 10/2016 | Huppert et al. |
| 2016/0302729 A1 | 10/2016 | Starr et al. |
| 2016/0310023 A1 | 10/2016 | Chachisvilis et al. |
| 2016/0317057 A1 | 11/2016 | Li et al. |
| 2016/0331263 A1 | 11/2016 | Cailler et al. |
| 2016/0331322 A1 | 11/2016 | Son et al. |
| 2016/0338591 A1 | 11/2016 | Lachenbruch et al. |
| 2016/0354001 A1 | 12/2016 | Buckley et al. |
| 2016/0367189 A1 | 12/2016 | Aimone et al. |
| 2016/0367192 A1 | 12/2016 | Iyengar et al. |
| 2016/0367406 A1 | 12/2016 | Barnett |
| 2017/0000407 A1 | 1/2017 | Saxby et al. |
| 2017/0007853 A1 | 1/2017 | Alford et al. |
| 2017/0027498 A1 | 2/2017 | Larson et al. |
| 2017/0079740 A1 | 3/2017 | Hufnagel et al. |
| 2017/0086519 A1 | 3/2017 | Vigano'et al. |

(56) References Cited

U.S. PATENT DOCUMENTS

| | | |
|---|---|---|
| 2017/0086709 A1 | 3/2017 | Khine et al. |
| 2017/0095208 A1 | 4/2017 | Oberleitner et al. |
| 2017/0146474 A1 | 5/2017 | Bedell et al. |
| 2017/0156594 A1 | 6/2017 | Stivoric et al. |
| 2017/0156621 A1 | 6/2017 | Bettinger et al. |
| 2017/0156658 A1 | 6/2017 | Maharbiz et al. |
| 2017/0164865 A1 | 6/2017 | Rafferty et al. |
| 2017/0164876 A1 | 6/2017 | Hyde et al. |
| 2017/0172439 A1 | 6/2017 | Zhu et al. |
| 2017/0202711 A1 | 7/2017 | Cernasov et al. |
| 2017/0224271 A1 | 8/2017 | Lachenbruch et al. |
| 2017/0231015 A1 | 8/2017 | Jang et al. |
| 2017/0258972 A1 | 9/2017 | Weston |
| 2017/0319075 A1 | 11/2017 | Homan et al. |
| 2017/0326004 A1 | 11/2017 | Long et al. |
| 2017/0367644 A1 | 12/2017 | Sharman et al. |
| 2018/0008177 A1 | 1/2018 | Shimuta et al. |
| 2018/0055359 A1 | 3/2018 | Shamim et al. |
| 2018/0055697 A1 | 3/2018 | Mihali et al. |
| 2018/0056087 A1 | 3/2018 | Ribeiro et al. |
| 2018/0070880 A1 | 3/2018 | Trembly et al. |
| 2018/0074547 A1 | 3/2018 | Smadi et al. |
| 2018/0116877 A1 | 5/2018 | Ineichen |
| 2018/0132287 A1 | 5/2018 | Cheng et al. |
| 2018/0192514 A1 | 7/2018 | Seo |
| 2018/0200414 A1 | 7/2018 | Askem et al. |
| 2018/0206758 A1 | 7/2018 | Feldkamp et al. |
| 2018/0235484 A1 | 8/2018 | Mozdzierz |
| 2018/0296397 A1 | 10/2018 | Askem et al. |
| 2019/0021911 A1 | 1/2019 | Askem et al. |
| 2019/0060126 A1 | 2/2019 | Ribble et al. |
| 2019/0076298 A1 | 3/2019 | Quintanar et al. |
| 2019/0083025 A1 | 3/2019 | Aung et al. |
| 2019/0133812 A1 | 5/2019 | Seres et al. |
| 2019/0159938 A1 | 5/2019 | Askem et al. |
| 2019/0175098 A1 | 6/2019 | Burns |
| 2019/0192066 A1 | 6/2019 | Schoess et al. |
| 2019/0231939 A1 | 8/2019 | Askem et al. |
| 2019/0290496 A1 | 9/2019 | Brownhill et al. |
| 2019/0374387 A1 | 12/2019 | Ribble et al. |
| 2020/0054218 A1 | 2/2020 | Xi |
| 2020/0078482 A1 | 3/2020 | Yoon et al. |
| 2020/0147407 A1 | 5/2020 | Efremkin |
| 2020/0330258 A1 | 10/2020 | Hansen et al. |
| 2021/0212855 A1 | 7/2021 | Hansen et al. |
| 2022/0079814 A1 | 3/2022 | Chen et al. |

FOREIGN PATENT DOCUMENTS

| | | | |
|---|---|---|---|
| CN | 106102322 A | | 11/2016 |
| DE | 102012211015 A1 | | 1/2014 |
| DE | 102013013013 A1 | | 2/2015 |
| EP | 0369374 A2 | | 5/1990 |
| EP | 1418798 A2 | | 5/2004 |
| EP | 2454990 A2 | | 5/2012 |
| EP | 2565630 A1 | | 3/2013 |
| EP | 3060034 A1 | | 8/2016 |
| EP | 3231478 A1 | | 10/2017 |
| EP | 3409190 A1 | | 12/2018 |
| EP | 3499510 A1 | | 6/2019 |
| EP | 3837520 A1 | | 6/2021 |
| GB | 1476894 A | | 6/1977 |
| GB | 2316171 A | | 2/1998 |
| GB | 2563602 A | | 12/2018 |
| JP | 2008153179 A | | 7/2008 |
| JP | 2009-225863 A | | 10/2009 |
| KR | 20120119523 A | | 10/2012 |
| KR | 101224629 B1 | | 1/2013 |
| KR | 20140024743 A | | 3/2014 |
| KR | 20140058041 A | | 5/2014 |
| KR | 20160071044 A | | 6/2016 |
| KR | 20190105898 A | | 9/2019 |
| NL | 1027236 C2 | | 4/2006 |
| WO | WO 00/21433 A1 | | 4/2000 |
| WO | WO 00/43046 A2 | | 7/2000 |
| WO | WO 03/067229 A1 | | 8/2003 |
| WO | WO 2006/041997 A2 | | 4/2006 |
| WO | WO-2007013049 A1 | | 2/2007 |
| WO | WO 2007/030379 A2 | | 3/2007 |
| WO | WO 2008/006150 A1 | | 1/2008 |
| WO | WO 2008/010604 A1 | | 1/2008 |
| WO | WO 2009/052607 A1 | | 4/2009 |
| WO | WO 2009/089390 A2 | | 7/2009 |
| WO | WO 2009/120951 A2 | | 10/2009 |
| WO | WO 2009/141777 A1 | | 11/2009 |
| WO | WO 2010/020919 A1 | | 2/2010 |
| WO | WO 2010/105053 A2 | | 9/2010 |
| WO | WO-2010099507 A1 | | 9/2010 |
| WO | WO 2011/082420 A1 | | 7/2011 |
| WO | WO 2011/113070 A1 | | 9/2011 |
| WO | WO 2011/123848 A1 | | 10/2011 |
| WO | WO 2012/141999 A1 | | 10/2012 |
| WO | WO-2013007973 A2 | | 1/2013 |
| WO | WO 2013/026999 A1 | | 2/2013 |
| WO | WO 2013/044226 A2 | | 3/2013 |
| WO | WO 2014/036577 A1 | | 3/2014 |
| WO | WO-2014116816 A1 | | 7/2014 |
| WO | WO-2014140578 A1 | | 9/2014 |
| WO | WO 2015/112095 A1 | | 7/2015 |
| WO | WO 2015/168720 A1 | | 11/2015 |
| WO | WO 2016/025438 A1 | | 2/2016 |
| WO | WO 2016/030752 A1 | | 3/2016 |
| WO | WO 2016/058032 A1 | | 4/2016 |
| WO | WO-2016073777 A1 | | 5/2016 |
| WO | WO 2016/100218 A1 | | 6/2016 |
| WO | WO 2016/109744 A1 | | 7/2016 |
| WO | WO 2016/110564 A1 | | 7/2016 |
| WO | WO 2016/187136 A1 | | 11/2016 |
| WO | WO 2016/205872 A1 | | 12/2016 |
| WO | WO 2016/205881 A1 | | 12/2016 |
| WO | WO 2017/021006 A1 | | 2/2017 |
| WO | WO 2017/021965 A2 | | 2/2017 |
| WO | WO 2017/033058 A1 | | 3/2017 |
| WO | WO 2017/037479 A1 | | 3/2017 |
| WO | WO 2017/041014 A1 | | 3/2017 |
| WO | WO 2017/041385 A1 | | 3/2017 |
| WO | WO 2017/041386 A1 | | 3/2017 |
| WO | WO 2017/041387 A1 | | 3/2017 |
| WO | WO 2017/119996 A1 | | 7/2017 |
| WO | WO 2017/205728 A1 | | 11/2017 |
| WO | WO 2017/214188 A1 | | 12/2017 |
| WO | WO 2018/035612 A1 | | 3/2018 |
| WO | WO 2018/060417 A1 | | 4/2018 |
| WO | WO 2018/064569 A1 | | 4/2018 |
| WO | WO 2018/115461 A1 | | 6/2018 |
| WO | WO 2018/144938 A1 | | 8/2018 |
| WO | WO 2018/144941 A1 | | 8/2018 |
| WO | WO 2018/144943 A1 | | 8/2018 |
| WO | WO 2018/144946 A1 | | 8/2018 |
| WO | WO 2018/162728 A2 | | 9/2018 |
| WO | WO 2018/162732 A1 | | 9/2018 |
| WO | WO 2018/162735 A1 | | 9/2018 |
| WO | WO 2018/162736 A1 | | 9/2018 |
| WO | WO 2018/185138 A1 | | 10/2018 |
| WO | WO 2018/189265 A1 | | 10/2018 |
| WO | WO 2018/209090 A1 | | 11/2018 |
| WO | WO 2018/210692 A1 | | 11/2018 |
| WO | WO 2018/210693 A1 | | 11/2018 |
| WO | WO 2018/211458 A1 | | 11/2018 |
| WO | WO 2018/234443 A1 | | 12/2018 |
| WO | WO 2019/020550 A2 | | 1/2019 |
| WO | WO 2019/020551 A1 | | 1/2019 |
| WO | WO 2019/020666 A1 | | 1/2019 |
| WO | WO 2019/030384 A2 | | 2/2019 |
| WO | WO 2019/048624 A1 | | 3/2019 |
| WO | WO 2019/048626 A1 | | 3/2019 |
| WO | WO 2019/048638 A1 | | 3/2019 |
| WO | WO 2019/063481 A1 | | 4/2019 |
| WO | WO 2019/063488 A2 | | 4/2019 |
| WO | WO 2019/067264 A1 | | 4/2019 |
| WO | WO 2019/072531 A1 | | 4/2019 |
| WO | WO 2019/076967 A2 | | 4/2019 |
| WO | WO 2019/096828 A1 | | 5/2019 |
| WO | WO 2019/140441 A2 | | 7/2019 |

(56) References Cited

FOREIGN PATENT DOCUMENTS

| WO | WO 2019/140444 A1 | 7/2019 |
|---|---|---|
| WO | WO 2019/140448 A1 | 7/2019 |
| WO | WO 2019/140449 A1 | 7/2019 |
| WO | WO-2019193141 A1 | 10/2019 |
| WO | WO-2019216883 A1 | 11/2019 |
| WO | WO-2019230183 A1 | 12/2019 |
| WO | WO-2019238180 A1 | 12/2019 |
| WO | WO-2019238181 A1 | 12/2019 |
| WO | WO-2019238182 A1 | 12/2019 |
| WO | WO-2019238195 A1 | 12/2019 |
| WO | WO-2019238196 A1 | 12/2019 |
| WO | WO-2019238197 A1 | 12/2019 |
| WO | WO-2019238198 A1 | 12/2019 |
| WO | WO-2020043806 A1 | 3/2020 |

OTHER PUBLICATIONS

International Search Report and Written Opinion for Application No. PCT/EP2018/074180, dated Nov. 16, 2018, 12 pages.

Aubakir B., et al., "Vital Sign Monitoring Utilizing Eulerian Video Magnification and Thermography," 38th Annual International Conference of the IEEE Engineering in Medicine and Biology Society, Aug. 16, 2016, pp. 3527-3530 (4 pages).

Cauwe M., et al., "Technology Development for a Low-Cost, Roll-to-Roll Chip Embedding Solution Based on PET Foils," 18th European Microelectronics and Packaging Conference (EMPC), IEEE, Sep. 12, 2011, 6 pages.

Farooqui M., et al., "Low Cost Inkjet Printed Smart Bandage for Wirless Monitoring of Chronic Wounds," Scientific Reports, vol. 6, Jun. 29, 2016, 14 pages.

Geng Y., et al., "A Hybrid Low Power Biopatch for Body Surface Potential Measurement," IEEE Journal of Biomedical and Health Informatics, vol. 17 (3), May 1, 2013, pp. 591-599.

Iannetta Jr. R.A., et al., "Successful Case Histories of Polymer Based Circuitry on Flexible Film Substrates," Electro/94 International Conference Proceedings Combined Volumes, IEEE, XP010149465, May 10-12, 1994, pp. 885-889.

Jinto G., et al., "Reliability of Plastic-Encapsulated Electronic Components in Supersaturated Steam Environments," IEEE Transactions on Components, Packaging and Manufacturing Technology, vol. 5 (10), Oct. 2015, pp. 1423-1431.

Little Miss Plasters, kidstravelclub.co.uk., retrieved from http://www.kidstravelclub.co.uk/little-miss-girls-childrens-plasters on Aug. 26, 2016, 2 pages.

Lu B., et al., "A Study of the Autofluorescence of Parylene Materials for μTAS Applications," Lab on Chip, vol. 10 (14), Jul. 2010, pp. 1826-1834.

McLeod A.J., et al., "Motion Magnification for Endoscopic Surgery," Progress in Biomedical Optics and Imaging, SPIE—International Society for Optical Engineering, Mar. 12, 2014, vol. 9036, 8 pages.

Mostafalu P., et al., "Wireless Flexible Smart Bandage for Continuous Monitoring of Wound Oxygenation," IEEE Transactions on Biomedical Circuits and Systems, vol. 9 (5), Oct. 2015, pp. 670-677 (8 pages).

Narusawa H., "The Corona Discharge Causes Short Destruction that had Bad Influence on a Power Switching Circuit," Adphox Corporation, Jan. 1, 2009, retrieved from http://www.adphox.co.jp/keisokuki/ke-english-corona/CORONA_DISCHARGE_EN.pdf, 12 pages.

Raviglione A., et al., "Real-Time Smart Textile-Based System to Monitor Pressure Offloading of Diabetic Foot Ulcers," Journal of Diabetes Science and Technology, vol. 11 (5), Sep. 2017, pp. 894-898.

Rose D.P., et al., "Adhesive RFID Sensor Patch for Monitoring of Sweat Electrolytes," IEEE Transactions on Biomedical Engineering, vol. 62 (6), Jun. 2015, first published on Nov. 11, 2015, pp. 1457-1465.

Wakita J., et al., "Variations in Optical Absorption and Fluorescence Spectra for Polyimide Thin Films Caused by Structural Isomerism," Journal of Photopolymer Science and Technology, Jan. 1, 2003, 1 page.

Willis B., "Conformal Coating Inspection & Coating Faults," Vision Engineering, Jul. 21, 2016, retrieved from http://www.visioneng.com/wp-content/uploads/2017/11/Confirmal-Coating-Inspection-and-Defects.21JUL16.pdf, 35 pages.

Willis B., "Guide to Conformal Coating & Cleaning Defects Contents," Mar. 1, 2014, retrieved from http://coatingguide.smartgroup.org/Files%20pdf/Coating%20Defects%20V2%2014March2014.pdf, vol. 1, 31 pages.

International Preliminary Report on Patentability for Application No. PCT/EP2018/074180, dated Mar. 19, 2020, 10 pages.

Mehmood N., et al., "Applications of Modern Sensors and Wireless Technology in Effective Wound Management: Modern Sensors and Wireless Technology," Journal of Biomedical Materials Research Part B, vol. 102, May 1, 2014, XP055739544, pp. 885-895.

* cited by examiner

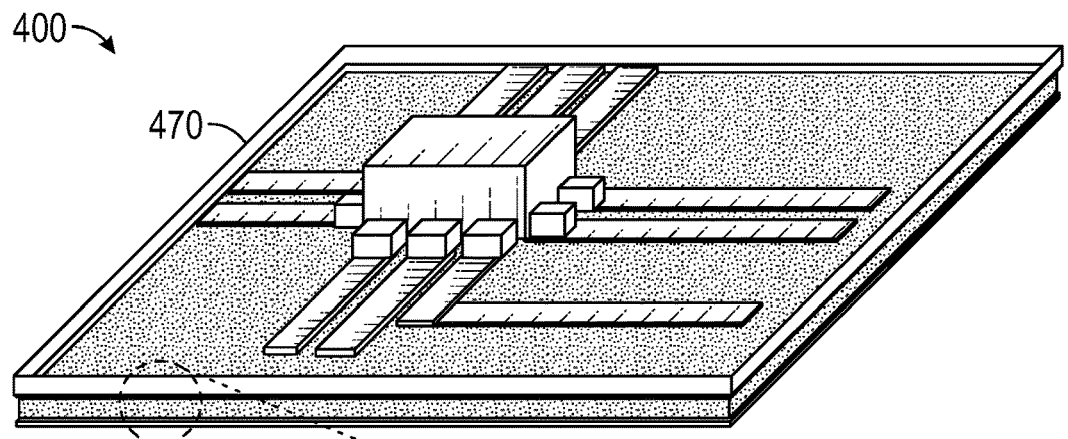
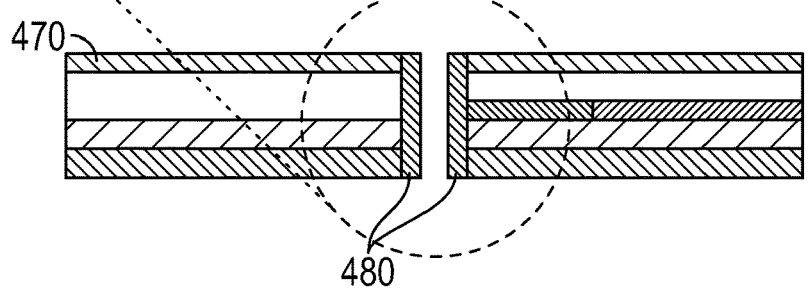
FIG. 4G
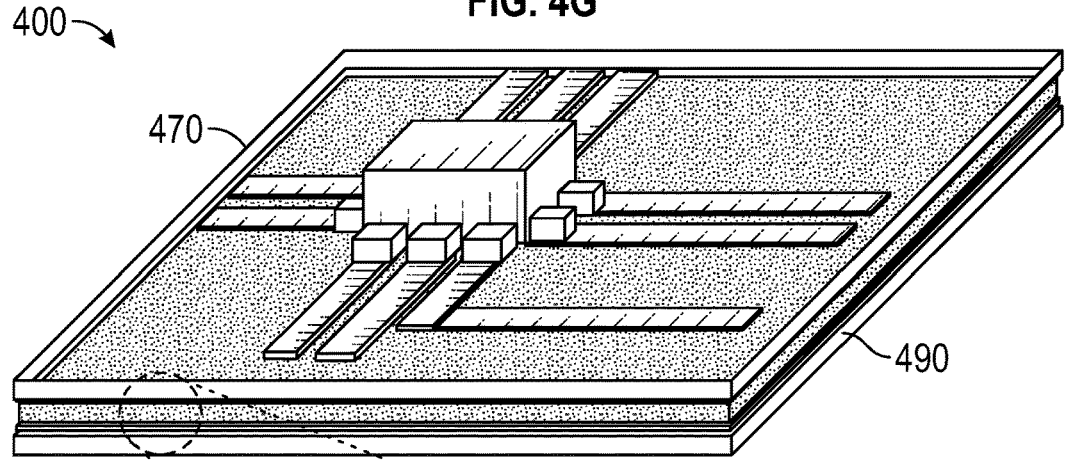
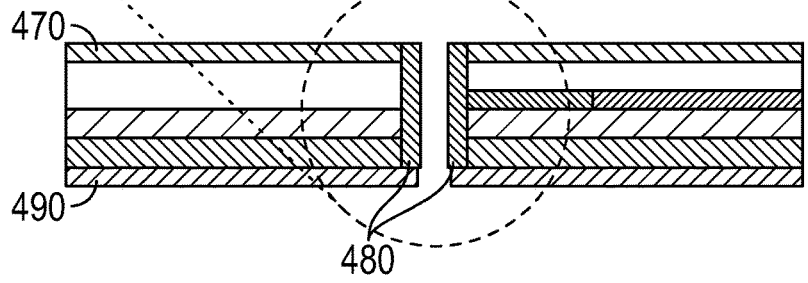
FIG. 4H

ELECTROSTATIC DISCHARGE PROTECTION FOR SENSORS IN WOUND THERAPY

CROSS-REFERENCE TO RELATED APPLICATIONS

This application is a U.S. national stage application of International Patent Application No. PCT/EP2018/074180, filed Sep. 7, 2018, which claims the benefit of U.S. Provisional Application No. 62/556,450, filed Sep. 10, 2017, and U.K. Provisional Application No. 1804971.8, filed Mar. 28, 2018; the disclosures of which are hereby incorporated by reference in their entirety.

BACKGROUND

Field

Embodiments of the present disclosure relate to apparatuses, systems, and methods for the treatment of wounds, for example using dressings in combination with negative pressure wound therapy or non-negative pressure wound therapy.

Description of the Related Art

Many different types of wound dressings are known for aiding in the healing process of a human or animal. These different types of wound dressings include many different types of materials and layers, for example, gauze, pads, foam pads or multi-layer wound dressings. Topical negative pressure therapy, sometimes referred to as vacuum assisted closure, negative pressure wound therapy, or reduced pressure wound therapy, is widely recognized as a beneficial mechanism for improving the healing rate of a wound. Such therapy is applicable to a broad range of wounds such as incisional wounds, open wounds and abdominal wounds or the like.

SUMMARY

In some embodiments, an apparatus is disclosed for use in monitoring or treating a wound. The apparatus can include a wound dressing, a circuit board, and a sensor. The wound dressing can be positioned over a wound of a patient and absorb wound exudate from the wound. The circuit board can be incorporated in or coupled to the wound dressing and include a first conductive pathway extending around at least part of a perimeter of a first side of the circuit board. The first conductive pathway can be electrically coupled to an electrical ground for the circuit board. The sensor can be mounted on the circuit board and output a signal usable to determine a value indicative of a physiological parameter of the patient. The first conductive pathway can protect the sensor against an electrostatic discharge.

The apparatus of the preceding paragraph can include one or more of the following features: The circuit board can be a flexible printed circuit board. The circuit board can be stretchable. The circuit board can include conductive tracks on an elastomer substrate and a conformal coating on the elastomer substrate. The circuit board can include a second conductive pathway extending around at least part of a perimeter of a second side of the circuit board opposite the first side, and the second conductive pathway can be electrically coupled to the electrical ground and configured to protect the sensor against the electrostatic discharge. The apparatus can further include multiple vias electrically connecting the first conductive pathway and the second conductive pathway through the circuit board. The first conductive pathway can extend around at least half of the perimeter of the first side. The first conductive pathway can extend around at least 75% of the perimeter of the first side. The sensor can continue to output the signal subsequent to the wound dressing being exposed to a defibrillation shock. The circuit board can be incorporated in a wound contact layer of the wound dressing. The sensor can include one or more of a temperature sensor, an impedance sensor, an optical sensor, or a $SpO_2$ sensor. The apparatus can further include a controller configured to receive the signal, determine the value, and output the value for presentation. The controller may not be mounted on the circuit board.

In some embodiments, a method is disclosed for manufacturing an apparatus for use in monitoring or treating a wound. The method can include: mounting a sensor on a substrate and in electrical communication with conductive tracks on the substrate; applying a conformal coating to the substrate; perforating the substrate; adding a first conductive pathway extending around at least part of a perimeter of a first side of the substrate; electrically connecting the first conductive pathway to an electrical ground for the sensor; and incorporating the substrate into a wound dressing or coupling the substrate to the wound dressing.

The method of the preceding paragraph can include one or more of the following features: The sensor can output a signal usable to determine a value indicative of a physiological parameter of a patient when the sensor is positioned proximate to the patient. The adding can include dipping or overmolding the first conductive pathway on the substrate. The substrate can include thermoplastic polyurethane. The applying can include applying the conformal coating to the first side and a second side of the substrate opposite the first side. The method can further include: adding a second conductive pathway extending around at least part of a perimeter of a second side of the substrate opposite the first side; and electrically connecting the second conductive pathway to the electrical ground. The method can further include electrically connecting the first conductive pathway to the second conductive pathway through the substrate. The method can further include electrically connecting the first conductive pathway to the second conductive pathway around an edge of the substrate.

BRIEF DESCRIPTION OF THE DRAWINGS

Embodiments of the present disclosure will now be described hereinafter, by way of example only, with reference to the accompanying drawings in which:

FIGS. 4A-4H illustrate a process for constructing a sensor array according to some embodiments;

DETAILED DESCRIPTION

Figure 1:
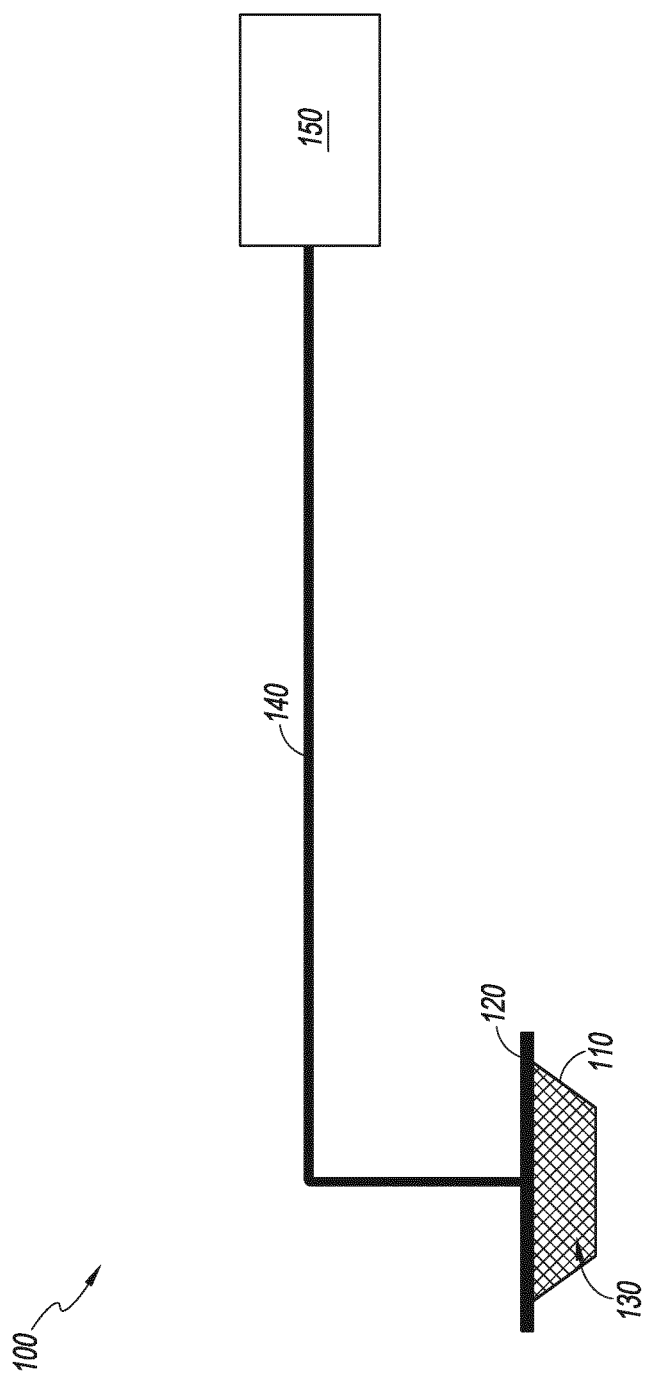
FIG. 1 illustrates a wound treatment system according to some embodiments.

Embodiments disclosed herein relate to apparatuses and methods of treating a wound with or without reduced pressure, including for example a source of negative pressure and wound dressing components and apparatuses. The apparatuses and components comprising the wound overlay and packing materials or internal layers, if any, are sometimes collectively referred to herein as wound dressings. In some embodiments, the wound dressing can be provided to be utilized without reduced pressure.

Some embodiments disclosed herein relate to wound therapy for a human or animal body. Therefore, any reference to a wound herein can refer to a wound on a human or animal body, and any reference to a body herein can refer to a human or animal body.

The disclosed embodiments may relate to preventing or minimizing damage to physiological tissue or living tissue, or to the treatment of damaged tissue (for example, a wound as described herein).

As used herein the expression "wound" may include an injury to living tissue may be caused by a cut, blow, or other impact, typically one in which the skin is cut or broken. A wound may be a chronic or acute injury. Acute wounds occur as a result of surgery or trauma. They move through the stages of healing within a predicted timeframe. Chronic wounds typically begin as acute wounds. The acute wound can become a chronic wound when it does not follow the healing stages resulting in a lengthened recovery. It is believed that the transition from acute to chronic wound can be due to a patient being immuno-compromised.

Chronic wounds may include for example: venous ulcers (such as those that occur in the legs), which account for the majority of chronic wounds and mostly affect the elderly, diabetic ulcers (for example, foot or ankle ulcers), peripheral arterial disease, pressure ulcers, or epidermolysis bullosa (EB).

Examples of other wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, diabetic ulcers, pressure ulcers, stoma, surgical wounds, trauma, and venous ulcers or the like.

Wounds may also include a deep tissue injury. Deep tissue injury is a term proposed by the National Pressure Ulcer Advisory Panel (NPUAP) to describe a unique form of pressure ulcers. These ulcers have been described by clinicians for many years with terms such as purple pressure ulcers, ulcers that are likely to deteriorate and bruises on bony prominences.

Wound may also include tissue at risk of becoming a wound as discussed herein. For example, tissue at risk may include tissue over a bony protuberance (at risk of deep tissue injury/insult) or pre-surgical tissue (for example, knee tissue) that may has the potential to be cut (for example, for joint replacement/surgical alteration/reconstruction).

Some embodiments relate to methods of treating a wound with the technology disclosed herein in conjunction with one or more of the following: advanced footwear, turning a patient, offloading (such as, offloading diabetic foot ulcers), treatment of infection, systemix, antimicrobial, antibiotics, surgery, removal of tissue, affecting blood flow, physiotherapy, exercise, bathing, nutrition, hydration, nerve stimulation, ultrasound, electrostimulation, oxygen therapy, microwave therapy, active agents ozone, antibiotics, antimicrobials, or the like.

Alternatively or additionally, a wound may be treated using topical negative pressure ("TNP") or traditional advanced wound care, which is not aided by the using of applied negative pressure (may also be referred to as non-negative pressure therapy).

Advanced wound care may include use of an absorbent dressing, an occlusive dressing, use of an antimicrobial or debriding agents in a wound dressing or adjunct, a pad (for example, a cushioning or compressive therapy, such as stockings or bandages), or the like.

In some embodiments, treatment of such wounds can be performed using traditional wound care, wherein a dressing can be applied to the wound to facilitate and promote healing of the wound.

Some embodiments relate to methods of manufacturing a wound dressing comprising providing a wound dressing as disclosed herein.

The wound dressings that may be utilized in conjunction with the disclosed technology include any known dressing in the art. The technology is applicable to negative pressure therapy treatment as well as non-negative pressure therapy treatment.

In some embodiments, a wound dressing comprises one or more absorbent layer(s). The absorbent layer may be a foam or a superabsorbent.

In some embodiments, wound dressings may comprise a dressing layer including a polysaccharide or modified polysaccharide, a polyvinylpyrrolidone, a polyvinyl alcohol, a polyvinyl ether, a polyurethane, a polyacrylate, a polyacrylamide, collagen, or gelatin or mixtures thereof. Dressing layers comprising the polymers listed are known in the art as being useful for forming a wound dressing layer for either negative pressure therapy or non-negative pressure therapy.

In some embodiments, the polymer matrix may be a polysaccharide or modified polysaccharide.

In some embodiments, the polymer matrix may be a cellulose. Cellulose material may include hydrophilically modified cellulose such as methyl cellulose, carboxymethyl cellulose (CMC), carboxymethyl cellulose (CEC), ethyl cellulose, propyl cellulose, hydroxyethyl cellulose, hydroxypropyl cellulose, hydroxypropylmethyl cellulose, carboxyethyl sulphonate cellulose, cellulose alkyl sulphonate, or mixtures thereof.

In certain embodiments, cellulose material may be cellulose alkyl sulphonate. The alkyl moiety of the alkyl sulphonate substituent group may have an alkyl group having 1 to 6 carbon atoms, such as methyl, ethyl, propyl, or butyl. The alkyl moiety may be branched or unbranched, and hence suitable propyl sulphonate substituents may be 1- or 2-methyl-ethylsulphonate. Butyl sulphonate substituents may be 2-ethyl-ethylsulphonate, 2,2-dimethyl-ethylsulphonate, or 1,2-dimethyl-ethylsulphonate. The alkyl sulphonate substituent group may be ethyl sulphonate. The cellulose alkyl sulphonate is described in WO10061225, US2016/114074, US2006/0142560, or U.S. Pat. No. 5,703,225, the disclosures of which are hereby incorporated by reference in their entirety.

Cellulose alkyl sulfonates may have varying degrees of substitution, the chain length of the cellulose backbone structure, and the structure of the alkyl sulfonate substituent.

Solubility and absorbency are largely dependent on the degree of substitution: as the degree of substitution is increased, the cellulose alkyl sulfonate becomes increasingly soluble. It follows that, as solubility increases, absorbency increases.

In some embodiments, a wound dressing also comprises a top or cover layer.

The thickness of the wound dressing disclosed herein may be between 1 to 20, or 2 to 10, or 3 to 7 mm.

Non-Negative Pressure Wound Dressing

In some embodiments, the disclosed technology may be used in conjunction with a non-negative pressure dressing. A non-negative pressure wound dressing suitable for providing protection at a wound site may comprise an absorbent layer for absorbing wound exudate and an obscuring element for at least partially obscuring a view of wound exudate absorbed by the absorbent layer in use.

The obscuring element may be partially translucent.

The obscuring element may be a masking layer.

The non-negative pressure wound dressing may further comprise a region in or adjacent the obscuring element for allowing viewing of the absorbent layer. For example, the obscuring element layer may be provided over a central region of the absorbent layer and not over a border region of the absorbent layer. In some embodiments, the obscuring element is of hydrophilic material or is coated with a hydrophilic material.

The obscuring element may comprise a three-dimensional knitted spacer fabric. The spacer fabric is known in the art and may include a knitted spacer fabric layer.

The obscuring element may further comprise an indicator for indicating the need to change the dressing.

In some embodiments, the obscuring element is provided as a layer at least partially over the absorbent layer, further from a wound site than the absorbent layer in use.

The non-negative pressure wound dressing may further comprise a plurality of openings in the obscuring element for allowing fluid to move therethrough. The obscuring element may comprise, or may be coated with, a material having size-exclusion properties for selectively permitting or preventing passage of molecules of a predetermined size or weight.

The obscuring element may be configured to at least partially mask light radiation having wavelength of 600 nm and less.

The obscuring element may be configured to reduce light absorption by 50% or more.

The obscuring element may be configured to yield a CIE L* value of 50 or more, and optionally 70 or more. In some embodiments, the obscuring element may be configured to yield a CIE L* value of 70 or more.

In some embodiments, the non-negative pressure wound dressing may further comprise at least one of a wound contact layer, a foam layer, an odor control element, a pressure-resistant layer and a cover layer.

In some embodiments, the cover layer is present, and the cover layer is a translucent film Typically, the translucent film has a moisture vapour permeability of 500 g/m²/24 hours or more.

The translucent film may be a bacterial bather.

In some embodiments, the non-negative pressure wound dressing as disclosed herein comprises the wound contact layer and the absorbent layer overlies the wound contact layer. The wound contact layer carries an adhesive portion for forming a substantially fluid tight seal over the wound site.

The non-negative pressure wound dressing as disclosed herein may comprise the obscuring element and the absorbent layer being provided as a single layer.

In some embodiments, the non-negative pressure wound dressing disclosed herein comprises the foam layer, and the obscuring element is of a material comprising components that may be displaced or broken by movement of the obscuring element.

In some embodiments, the non-negative pressure wound dressing comprises an odor control element, and in another embodiment the dressing does not include an odor control element. When present, the odor control element may be dispersed within or adjacent the absorbent layer or the obscuring element. Alternatively, when present the odor control element may be provided as a layer sandwiched between the foam layer and the absorbent layer.

In some embodiments, the disclosed technology for a non-negative pressure wound dressing comprises a method of manufacturing a wound dressing, comprising: providing an absorbent layer for absorbing wound exudate; and providing an obscuring element for at least partially obscuring a view of wound exudate absorbed by the absorbent layer in use.

In some embodiments, the non-negative pressure wound dressing is may be suitable for providing protection at a wound site, comprising: an absorbent layer for absorbing wound exudate; and a shielding layer provided over the absorbent layer, and further from a wound-facing side of the wound dressing than the absorbent layer. The shielding layer may be provided directly over the absorbent layer. In some embodiments, the shielding layer comprises a three-dimensional spacer fabric layer.

The shielding layer increases the area over which a pressure applied to the dressing is transferred by 25% or more or the initial area of application. For example the shielding layer increases the area over which a pressure applied to the dressing is transferred by 50% or more, and optionally by 100% or more, and optionally by 200% or more.

The shielding layer may comprise 2 or more sub-layers, wherein a first sub-layer comprises through holes and a further sub-layer comprises through holes and the through holes of the first sub-layer are offset from the through holes of the further sub-layer.

The non-negative pressure wound dressing as disclosed herein may further comprise a permeable cover layer for allowing the transmission of gas and vapour therethrough, the cover layer provided over the shielding layer, wherein through holes of the cover layer are offset from through holes of the shielding layer.

The non-negative pressure wound dressing may be suitable for treatment of pressure ulcers.

A more detailed description of the non-negative pressure dressing disclosed hereinabove is provided in WO2013007973, the entirety of which is hereby incorporated by reference.

In some embodiments, the non-negative pressure wound dressing may be a multi-layered wound dressing comprising: a fibrous absorbent layer for absorbing exudate from a wound site; and a support layer configured to reduce shrinkage of at least a portion of the wound dressing.

In some embodiments, the multi-layered wound dressing disclosed herein, further comprises a liquid impermeable film layer, wherein the support layer is located between the absorbent layer and the film layer.

The support layer disclosed herein may comprise a net. The net may comprise a geometric structure having a plurality of substantially geometric apertures extending therethrough. The geometric structure may for example comprise a plurality of bosses substantially evenly spaced and joined by polymer strands to form the substantially geometric apertures between the polymer strands.

The net may be formed from high density polyethylene.

The apertures may have an area from 0.005 to 0.32 mm$^2$.

The support layer may have a thickness of from 50 to 150 μm.

In some embodiments, the support layer is located directly adjacent the absorbent layer. Typically, the support layer is bonded to fibers in a top surface of the absorbent layer. The support layer may further comprise a bonding layer, wherein the support layer is heat laminated to the fibers in the absorbent layer via the bonding layer. The bonding layer may comprise a low melting point adhesive such as ethylene-vinyl acetate adhesive.

In some embodiments, the multi-layered wound dressing disclosed herein further comprises an adhesive layer attaching the film layer to the support layer.

In some embodiments, the multi-layered wound dressing disclosed herein further comprises a wound contact layer located adjacent the absorbent layer for positioning adjacent a wound. The multi-layered wound dressing may further comprise a fluid transport layer between the wound contact layer and the absorbent layer for transporting exudate away from a wound into the absorbent layer.

A more detailed description of the multi-layered wound dressing disclosed hereinabove is provided in GB patent application filed on 28 Oct. 2016 with application number GB1618298.2, the entirety of which is hereby incorporated by reference.

In some embodiments, the disclosed technology may be incorporated in a wound dressing comprising a vertically lapped material comprising: a first layer of an absorbing layer of material, and a second layer of material, wherein the first layer being constructed from at least one layer of non-woven textile fibers, the non-woven textile fibers being folded into a plurality of folds to form a pleated structure. In some embodiments, the wound dressing further comprises a second layer of material that is temporarily or permanently connected to the first layer of material.

Typically the vertically lapped material has been slitted.

In some embodiments, the first layer has a pleated structure having a depth determined by the depth of pleats or by the slitting width. The first layer of material may be a moldable, lightweight, fiber-based material, blend of material or composition layer.

The first layer of material may comprise one or more of manufactured fibers from synthetic, natural or inorganic polymers, natural fibers of a cellulosic, proteinaceous or mineral source.

The wound dressing may comprise two or more layers of the absorbing layer of material vertically lapped material stacked one on top of the other, wherein the two or more layers have the same or different densities or composition.

The wound dressing may in some embodiments, comprise only one layer of the absorbing layer of material vertically lapped material.

The absorbing layer of material is a blend of natural or synthetic, organic or inorganic fibers, and binder fibers, or bicomponent fibers typically PET with a low melt temperature PET coating to soften at specified temperatures and to act as a bonding agent in the overall blend.

In some embodiments, the absorbing layer of material may be a blend of 5 to 95% thermoplastic polymer, and 5 to 95 wt % of a cellulose or derivative thereof.

In some embodiments, the wound dressing disclosed herein has a second layer comprises a foam or a dressing fixative.

The foam may be a polyurethane foam. The polyurethane foam may have an open or closed pore structure.

The dressing fixative may include bandages, tape, gauze, or backing layer.

In some embodiments, the wound dressing as disclosed herein comprises the absorbing layer of material connected directly to a second layer by lamination or by an adhesive, and the second layer is connected to a dressing fixative layer. The adhesive may be an acrylic adhesive, or a silicone adhesive.

In some embodiments, the wound dressing as disclosed herein further comprises layer of a superabsorbent fiber, or a viscose fiber or a polyester fiber.

In some embodiments, the wound dressing as disclosed herein further comprises a backing layer. The backing layer may be a transparent or opaque film Typically the backing layer comprises a polyurethane film (typically a transparent polyurethane film).

A more detailed description of the multi-layered wound dressing disclosed hereinabove is provided in GB patent applications filed on 12 Dec. 2016 with application number GB1621057.7; and 22 Jun. 2017 with application number GB1709987.0, the entirety of each of which is hereby incorporated by reference.

In some embodiments, the non-negative pressure wound dressing may comprise an absorbent component for a wound dressing, the component comprising a wound contacting layer comprising gel forming fibers bound to a foam layer, wherein the foam layer is bound directly to the wound contact layer by an adhesive, polymer based melt layer, by flame lamination or by ultrasound.

The absorbent component may be in a sheet form.

The wound contacting layer may comprise a layer of woven or non-woven or knitted gel forming fibers.

The foam layer may be an open cell foam, or closed cell foam, typically an open cell foam. The foam layer is a hydrophilic foam.

The wound dressing may comprise the component that forms an island in direct contact with the wound surrounded by periphery of adhesive that adheres the dressing to the wound. The adhesive may be a silicone or acrylic adhesive, typically a silicone adhesive.

The wound dressing may be covered by a film layer on the surface of the dressing furthest from the wound.

A more detailed description of the wound dressing of this type hereinabove is provided in EP2498829, the entirety of which is hereby incorporated by reference.

In some embodiments, the non-negative pressure wound dressing may comprise a multi layered wound dressing for use on wounds producing high levels of exudate, characterized in that the dressing comprising: a transmission layer having an MVTR of at least 300 gm$^2$/24 hours, an absorbent core comprising gel forming fibers capable of absorbing and retaining exudate, a wound contacting layer comprising gel forming fibers which transmits exudate to the absorbent core and a keying layer positioned on the absorbent core, the absorbent core and wound contacting layer limiting the lateral spread of exudate in the dressing to the region of the wound.

The wound dressing may be capable of handling at least 6 g (or 8 g and 15 g) of fluid per 10 cm$^2$ of dressing in 24 hours.

The wound dressing may comprise gel forming fibers that are chemically modified cellulosic fibers in the form of a fabric. The fibers may include carboxymethylated cellulose fibers, typically sodium carboxymethylcellulose fiber.

The wound dressing may comprise a wound contact layer with a lateral wicking rate from 5 mm per minute to 40 mm per minute. The wound contact layer may have a fiber density between 25 gm$^2$ and 55 gm$^2$ such as 35 gm$^2$.

The absorbent core may have an absorbency of exudate of at least 10 g/g, and typically a rate of lateral wicking of less the 20 mm per minute.

The absorbent core may have a blend in the range of up to 25% cellulosic fibers by weight and 75% to 100% gel forming fibers by weight.

Alternatively, the absorbent core may have a blend in the range of up to 50% cellulosic fibers by weight and 50% to 100% gel forming fibers by weight. For example the blend is in the range of 50% cellulosic fibers by weight and 50% gel forming fibers by weight.

The fiber density in the absorbent core may be between 150 gm$^2$ and 250 gm$^2$, or about 200 gm$^2$.

The wound dressing when wet may have shrinkage that is less than 25% or less than 15% of its original size/dimension.

The wound dressing may comprise a transmission layer and the layer is a foam. The transmission layer may be a polyurethane foam laminated to a polyurethane film.

The wound dressing may comprise one or more layers selected from the group comprising a soluble medicated film layer; an odor-absorbing layer; a spreading layer and an additional adhesive layer.

The wound dressing may be 2 mm and 4 mm thick.

The wound dressing may be characterized in that the keying layer bonds the absorbent core to a neighboring layer. In some embodiments, the keying layer may be positioned on either the wound facing side of the absorbent core or the non-wound facing side of the absorbent core. In some embodiments, the keying layer is positioned between the absorbent core and the wound contact layer. The keying layer is a polyamide web.

A more detailed description of the wound dressing of this type hereinabove is provided in EP1718257, the entirety of which is hereby incorporated by reference.

In some embodiments, the non-negative pressure wound dressing may be a compression bandage. Compression bandages are known for use in the treatment of oedema and other venous and lymphatic disorders, e.g., of the lower limbs.

A compression bandage systems typically employ multiple layers including a padding layer between the skin and the compression layer or layers. The compression bandage may be useful for wounds such as handling venous leg ulcers.

The compression bandage in some embodiments may comprise a bandage system comprising an inner skin facing layer and an elastic outer layer, the inner layer comprising a first ply of foam and a second ply of an absorbent nonwoven web, the inner layer and outer layer being sufficiently elongated so as to be capable of being wound about a patient's limb. A compression bandage of this type is disclosed in WO99/58090, the entirety of which is hereby incorporated by reference.

In some embodiments, the compression bandage system comprises: a) an inner skin facing, elongated, elastic bandage comprising: (i) an elongated, elastic substrate, and (ii) an elongated layer of foam, said foam layer being affixed to a face of said substrate and extending 33% or more across said face of substrate in transverse direction and 67% or more across said face of substrate in longitudinal direction; and b) an outer, elongated, self-adhering elastic bandage; said bandage having a compressive force when extended; wherein, in use, said foam layer of the inner bandage faces the skin and the outer bandage overlies the inner bandage. A compression bandage of this type is disclosed in WO2006/110527, the entirety of which is hereby incorporated by reference.

In some embodiments, other compression bandage systems such as those disclosed in U.S. Pat. No. 6,759,566 and US 2002/0099318, the entirety of each of which is hereby incorporated by reference.

Negative Pressure Wound Dressing

Treatment of wounds can be performed using negative pressure wound therapy, wherein a reduced or negative pressure can be applied to the wound to facilitate and promote healing of the wound. The wound dressing and methods as disclosed herein may be applied to other parts of the body, and are not necessarily limited to monitoring, prevention, and treatment of wounds.

It will be understood that embodiments of the present disclosure are generally applicable to use in TNP therapy systems. Briefly, negative pressure wound therapy assists in the closure and healing of many forms of "hard to heal" wounds by reducing tissue oedema; encouraging blood flow and granular tissue formation; removing excess exudate and may reduce bacterial load (and thus infection risk). In addition, the therapy allows for less disturbance of a wound leading to more rapid healing. TNP therapy systems may also assist on the healing of surgically closed wounds by removing fluid and by helping to stabilize the tissue in the apposed position of closure. A further beneficial use of TNP therapy can be found in grafts and flaps where removal of excess fluid is important and close proximity of the graft to tissue is required in order to ensure tissue viability.

As is used herein, reduced or negative pressure levels, such as –X mmHg, represent pressure levels relative to normal ambient atmospheric pressure, which can correspond to 760 mmHg (or 1 atm, 29.93 inHg, 101.325 kPa, 14.696 psi, etc.). Accordingly, a negative pressure value of –X mmHg reflects absolute pressure that is X mmHg below 760 mmHg or, in other words, an absolute pressure of (760–X) mmHg In addition, negative pressure that is "less" or "smaller" than X mmHg corresponds to pressure that is closer to atmospheric pressure (such as, –40 mmHg is less than –60 mmHg). Negative pressure that is "more" or "greater" than –X mmHg corresponds to pressure that is further from atmospheric pressure (such as, –80 mmHg is more than –60 mmHg). In some embodiments, local ambient atmospheric pressure is used as a reference point, and such local atmospheric pressure may not necessarily be, for example, 760 mmHg.

The negative pressure range for some embodiments of the present disclosure can be approximately –80 mmHg, or between about –20 mmHg and –200 mmHg or more. Note that these pressures are relative to normal ambient atmospheric pressure, which can be 760 mmHg Thus, –200 mmHg would be about 560 mmHg in practical terms. In some embodiments, the pressure range can be between about –40 mmHg and –150 mmHg. Alternatively a pressure range of up to –75 mmHg, up to –80 mmHg or over –80 mmHg can be used. Also in other embodiments a pressure range of below −75 mmHg can be used. Alternatively, a pressure range of over approximately −100 mmHg, or even −150 mmHg, can be supplied by the negative pressure apparatus.

In some embodiments of wound closure devices described herein, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. Negative pressure may be varied over time for example using a sinusoidal wave, square wave, or in synchronization with one or more patient physiological indices (such as, heartbeat). Examples of such applications where additional disclosure relating to the preceding may be found include U.S. Pat. No. 8,235,955, titled "Wound treatment apparatus and method," issued on Aug. 7, 2012; and U.S. Pat. No. 7,753,894, titled "Wound cleansing apparatus with stress," issued Jul. 13, 2010. The disclosures of both of these patents are hereby incorporated by reference in their entirety.

Embodiments of the wound dressings, wound dressing components, wound treatment apparatuses and methods described herein may also be used in combination or in addition to those described in International Application No. PCT/IB2013/001469, filed May 22, 2013, published as WO 2013/175306 on Nov. 28, 2013, titled "APPARATUSES AND METHODS FOR NEGATIVE PRESSURE WOUND THERAPY," U.S. patent application Ser. No. 14/418,908, filed Jan. 30, 2015, published as US 2015/0190286 A1 on Jul. 9, 2015, titled "WOUND DRESSING AND METHOD OF TREATMENT," the disclosures of which are hereby incorporated by reference in their entireties. Embodiments of the wound dressings, wound dressing components, wound treatment apparatuses and methods described herein may also be used in combination or in addition to those described in U.S. patent application Ser. No. 13/092,042, filed Apr. 21, 2011, published as US2011/0282309, titled "WOUND DRESSING AND METHOD OF USE," and U.S. patent application Ser. No. 14/715,527, filed May 18, 2015, published as US2016/0339158 A1 on Nov. 24, 2016, titled "FLUIDIC CONNECTOR FOR NEGATIVE PRESSURE WOUND THERAPY," the disclosure of each of which are hereby incorporated by reference in its entirety, including further details relating to embodiments of wound dressings, the wound dressing components and principles, and the materials used for the wound dressings.

Additionally, some embodiments related to TNP wound treatment comprising a wound dressing in combination with a pump or associated electronics described herein may also be used in combination or in addition to those described in International Application PCT/EP2016/059329 filed Apr. 26, 2016, published as WO 2016/174048 on Nov. 3, 2016, entitled "REDUCED PRESSURE APPARATUS AND METHODS", the disclosure of which is hereby incorporated by reference in its entirety.

Wound Therapy System Overview

Systems for performing wound therapy, such as TNP therapy, can include one or more features that improve the tolerance of the systems to environmental conditions, such as electromagnetic radiation or electrostatic discharge (ESD). The improved tolerance of the systems can, for example, enable the systems to function despite non-ideal environmental conditions or function more safely in the presence of certain environmental conditions.

FIG. 1 illustrates an embodiment of a negative or reduced pressure wound treatment (or TNP) system 100 comprising a wound filler 130 placed inside a wound cavity 110, the wound cavity sealed by a wound cover 120. The wound filler 130 in combination with the wound cover 120 can be referred to as wound dressing. A single or multi lumen tube or conduit 140 is connected the wound cover 120 with a pump assembly 150 configured to supply reduced pressure. The wound cover 120 can be in fluidic communication with the wound cavity 110. In any of the system embodiments disclosed herein, as in the embodiment illustrated in FIG. 1, the pump assembly can be a canisterless pump assembly (meaning that exudate is collected in the wound dressing or is transferred via tube 140 for collection to another location). However, any of the pump assembly embodiments disclosed herein can be configured to include or support a canister. Additionally, in any of the system embodiments disclosed herein, any of the pump assembly embodiments can be mounted to or supported by the dressing, or adjacent to the dressing.

The wound filler 130 can be any suitable type, such as hydrophilic or hydrophobic foam, gauze, inflatable bag, and so on. The wound filler 130 can be conformable to the wound cavity 110 such that it substantially fills the cavity. The wound cover 120 can provide a substantially fluid impermeable seal over the wound cavity 110. The wound cover 120 can have a top side and a bottom side, and the bottom side adhesively (or in any other suitable manner) seals with wound cavity 110. The conduit 140 or lumen or any other conduit or lumen disclosed herein can be formed from polyurethane, PVC, nylon, polyethylene, silicone, or any other suitable material.

Some embodiments of the wound cover 120 can have a port (not shown) configured to receive an end of the conduit 140. For example, the port can be Renays Soft Port available from Smith & Nephew. In other embodiments, the conduit 140 can otherwise pass through or under the wound cover 120 to supply reduced pressure to the wound cavity 110 so as to maintain a desired level of reduced pressure in the wound cavity. The conduit 140 can be any suitable article configured to provide at least a substantially sealed fluid flow pathway between the pump assembly 150 and the wound cover 120, so as to supply the reduced pressure provided by the pump assembly 150 to wound cavity 110.

The wound cover 120 and the wound filler 130 can be provided as a single article or an integrated single unit. In some embodiments, no wound filler is provided and the wound cover 120 by itself may be considered the wound dressing. The wound dressing may then be connected, via the conduit 140, to a source of negative pressure, such as the pump assembly 150. The pump assembly 150 can be miniaturized and portable, although larger conventional pumps such can also be used.

The wound cover 120 can be located over a wound site to be treated. The wound cover 120 can form a substantially sealed cavity or enclosure over the wound site. In some embodiments, the wound cover 120 can be configured to have a film having a high water vapour permeability to enable the evaporation of surplus fluid, and can have a superabsorbing material contained therein to safely absorb wound exudate.

The pump assembly 150 can be configured to deliver negative pressure of approximately −80 mmHg, or between about −20 mmHg and 200 mmHg in some implementations. Note that these pressures are relative to normal ambient atmospheric pressure thus, −200 mmHg would be about 560 mmHg in practical terms. The pressure range can be between about −40 mmHg and −150 mmHg Alternatively a pressure range of up to −75 mmHg, up to −80 mmHg or over −80 mmHg can be used. Also a pressure range of below −75 mmHg can be used. Alternatively a pressure range of over approximately −100 mmHg, or In operation, the wound filler 130 is inserted into the wound cavity 110 and wound cover 120 is placed so as to seal the wound cavity 110. The pump assembly 150 provides a source of a negative pressure to the wound cover 120, which is transmitted to the wound cavity 110 via the wound filler 130. Fluid (such as, wound exudate) is drawn through the conduit 140, and can be stored in a canister. In some embodiments, fluid is absorbed by the wound filler 130 or one or more absorbent layers (not shown).

It will be appreciated that throughout this disclosure reference is made to a wound. The term wound is to be broadly construed and encompasses open and closed wounds in which skin is torn, cut or punctured or where trauma causes a contusion, or any other surficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, acute wounds, chronic wounds, surgical incisions and other incisions, sub-acute and dehisced wounds, traumatic wounds, flaps and skin grafts, lacerations, abrasions, contusions, burns, diabetic ulcers, pressure ulcers, stoma, surgical wounds, trauma and venous ulcers or the like. The components of the TNP system described herein can be particularly suited for incisional wounds that exude a small amount of wound exudate.

Wound Dressing Overview

Figure 2:
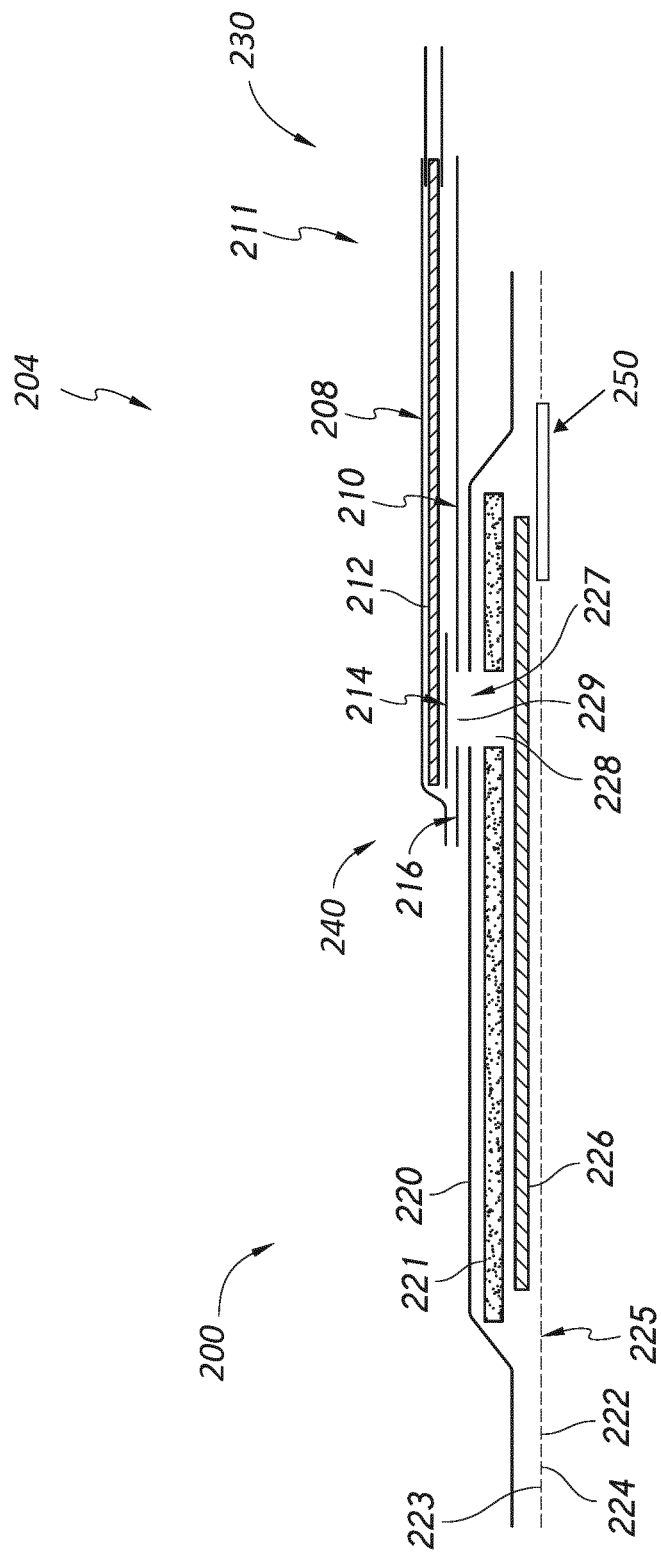
FIG. 2 illustrates a wound dressing and a fluidic connector according to some embodiments.

FIG. 2 illustrates a cross-section view of a wound dressing 200, which can be similar to or the same as the wound cover 120 and the wound filler 130 of FIG. 1, with a fluidic connector 204, which can be similar to or the same as the conduit 140 of FIG. 1. The wound dressing 200 can include a top or cover layer, or backing layer 220 attached to a wound contact layer 222, which can be joined or sealed together so as to define an interior space or chamber. This interior space or chamber may comprise additional structures that may be adapted to distribute or transmit negative pressure, store wound exudate and other fluids removed from the wound, and other functions. Examples of such structures include a transmission layer 226 and an absorbent layer 221 described herein. Moreover, one or more sensors 250, which can be part of a sensor array, can be incorporated onto or into the wound dressing 200, such as the wound contact layer 222 as illustrated.

As used herein the upper layer, top layer, or layer above refers to a layer farthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

The wound contact layer 222 can be a polyurethane layer or polyethylene layer or other flexible layer which is perforated, for example via a hot pin process, laser ablation process, ultrasound process or in some other way or otherwise made permeable to liquid and gas. The wound contact layer 222 has a lower surface 224 (for example, facing the wound) and an upper surface 223 (for example, facing away from the wound). The perforations 225 can comprise through holes in the wound contact layer 222 which enable fluid to flow through the wound contact layer 222. The wound contact layer 222 helps prevent tissue ingrowth into the other material of the wound dressing 200.

A porous layer 226 of porous material can be located above the wound contact layer 222. This porous layer, or transmission layer, 226 allows transmission of fluid including liquid and gas away from a wound site into upper layers of the wound dressing 200. In particular, the transmission layer 226 can ensure that an open air channel can be maintained to communicate negative pressure over the wound area even when the absorbent layer has absorbed substantial amounts of exudates.

A layer 221 of absorbent material is provided above the transmission layer 226. The absorbent material, which comprise a foam or non-woven natural or synthetic material, and which may optionally comprise a super-absorbent material, forms a reservoir for fluid, particularly liquid, removed from the wound site. In some embodiments, the layer 221 may also aid in drawing fluids towards the backing layer 220.

An aperture, hole, or orifice 227 is provided in the backing layer 220 to allow a negative pressure to be applied to the wound dressing 200. The fluidic connector 204 can be attached or sealed to the top of the backing layer 220 over the orifice 227 made into the wound dressing 200, and communicates negative pressure through the orifice 227.

In some embodiments, the absorbent layer 221 includes at least one through hole 228 located so as to underlie the fluidic connector 204. The through hole 228 may be the same size as the opening 227 in the backing layer, or may be bigger or smaller. The aperture or through-hole 228 can be provided in the absorbent layer 221 beneath the orifice 227 such that the orifice is connected directly to the transmission layer 226. This allows the negative pressure applied to the fluidic connector 204 to be communicated to the transmission layer 226 without passing through the absorbent layer 221. This ensures that the negative pressure applied to the wound site is not inhibited by the absorbent layer as it absorbs wound exudates. In other embodiments, no aperture may be provided in the absorbent layer 221, or alternatively a plurality of apertures underlying the orifice 227 may be provided.

Turning now to the fluidic connector 204, some embodiments include a sealing surface 216, a bridge 211 with a proximal end 230 and a distal end 240, and a filter 214. The sealing surface 216 can form the applicator previously described that is sealed to the top surface of the wound dressing 200. A bottom layer of the fluidic connector 204 may include the sealing surface 216. The fluidic connector 204 may further comprise an upper surface vertically spaced from the sealing surface 216, which in some embodiments is defined by a separate upper layer of the fluidic connector 204. In other embodiments the upper surface and the lower surface may be formed from the same piece of material. In some embodiments the sealing surface 216 may comprise at least one aperture 229 therein to communicate with the wound dressing 200.

The bridge 211 may include a first fluid passage 212 in communication with a source of negative pressure, the first fluid passage 212 comprising a porous material, such as a 3D knitted material, which may be the same or different than the porous layer 226. The bridge 211 can be encapsulated by at least one flexible film layer 208, 210 having a proximal and distal end and configured to surround the first fluid passage 212, the distal end of the flexible film being connected the sealing surface 216. The filter 214 is configured to substantially prevent wound exudate from entering the bridge Sensor-Enabled Wound Dressings A wound dressing, such as the wound dressing 200 of FIG. 2, can incorporate a number of sensors or sensors, such as the one or more sensors 250 of FIG. 2, to monitor characteristics of a wound as it heals. Collecting data from the wounds that heal well, and from those that do not, can provide useful insights towards identifying measurands to indicate whether a wound is on a healing trajectory.

A number of sensor technologies can be used in wound dressings or one or more components forming part of an overall wound dressing apparatus. For example, one or more sensors can be incorporated onto or into a wound contact layer, such as the wound contact layer 222 of FIG. 2, that can be placed in contact with the wound and allow fluid to pass through while causing little to no damage to the tissue in the wound. The sensor-integrated wound contact layer can be made of a flexible material such as silicone and can incorporate antimicrobials or other therapeutic agents. The sensor-integrated wound contact layer can incorporate adhesives that adhere to wet or dry tissue. In yet other implementations, the one or more sensors can additionally or alternatively be incorporated into or encapsulated within other components of the wound dressing, such as the absorbent layer or spacer layer.

In some implementations, the one or more sensors can include sensors for monitoring temperature (such as, 25 thermistor sensors, in a 5×5 array, ~20 mm pitch), pulse oximetry or SpO2 (such as, 4 or 5 SpO2 sensors, in a single line from the center of the wound contact layer to the edge thereof, 10 mm pitch), optical properties of the tissue, exudate, or foreign bodies (such as, 10 optical sensors, in 2×5 array, ~20 mm pitch; not all 5 sensors in each row of the array need be aligned), pH (such as, by measuring colour of a pH sensitive pad, optionally using the same optical sensors as for tissue colour), and impedance (such as, 9 impedance contacts, in a 3×3 array, ~40 mm pitch). Other sensors, such as pressure, flow, strain, colorimetric sensors configured to measure biological or chemical compounds (for example, dye coated colorimetric sensors) or the like, can be additionally or alternatively used. Colorimetric sensors can be used for measure odor, toxicity, etc. Any one or more sensors described herein can be placed or positioned to obtain measurements of any location in the wound or the skin.

The sensors can be supported by or incorporated onto a flexible or substantially flexible substrate, such as one or more of flexible or substantially flexible printed circuits (FPCs) which can be formed from flexible polymers including polyamide, polyimide (PI), polyester, polyethylene naphthalate (PEN), polyetherimide (PEI), polyurethane, thermoplastic polyurethane (TPU), along with various fluropolymers (FEP) and copolymers, or any other suitable material. Substantially flexible or flexible substrates can include single-sided, double-sided, or multi-layer circuits. In some implementations, the sensor array can be incorporated into a two-layer flexible circuit. In some embodiments, the FPC can be a multi-layer flexible printed circuit. In some embodiments, these flexible printed circuits can be incorporated into any layer of the wound dressing. In some embodiments, a flexible circuit can be incorporated into (for example, positioned on or in) a wound contact layer. For example, the flexible circuit can be incorporated into a wound contact layer similar to the wound contact layer described with reference to FIGS. 2B and 2C. The wound contact layer can have cutouts or slits that allow for one or more sensors to protrude out of the lower surface of the wound contact layer and contact the wound area directly.

The sensor-integrated wound contact layer can include a first and second wound contact layer with an FPC sandwiched between the two layers of wound contact layer material. The first wound contact layer has a lower surface intended to be in contact with the wound and an upper surface intended to be in contact with the FPC. The second wound contact layer has a lower surface intended to be in contact with the FPC and an upper surface intended to be in contact with a wound dressing or one or more components forming part of an overall wound dressing apparatus. The upper surface of the first wound contact layer and the lower surface of the second wound contact layer can be adhered together with the FPC sandwiched between the two layers.

Figure 3A:
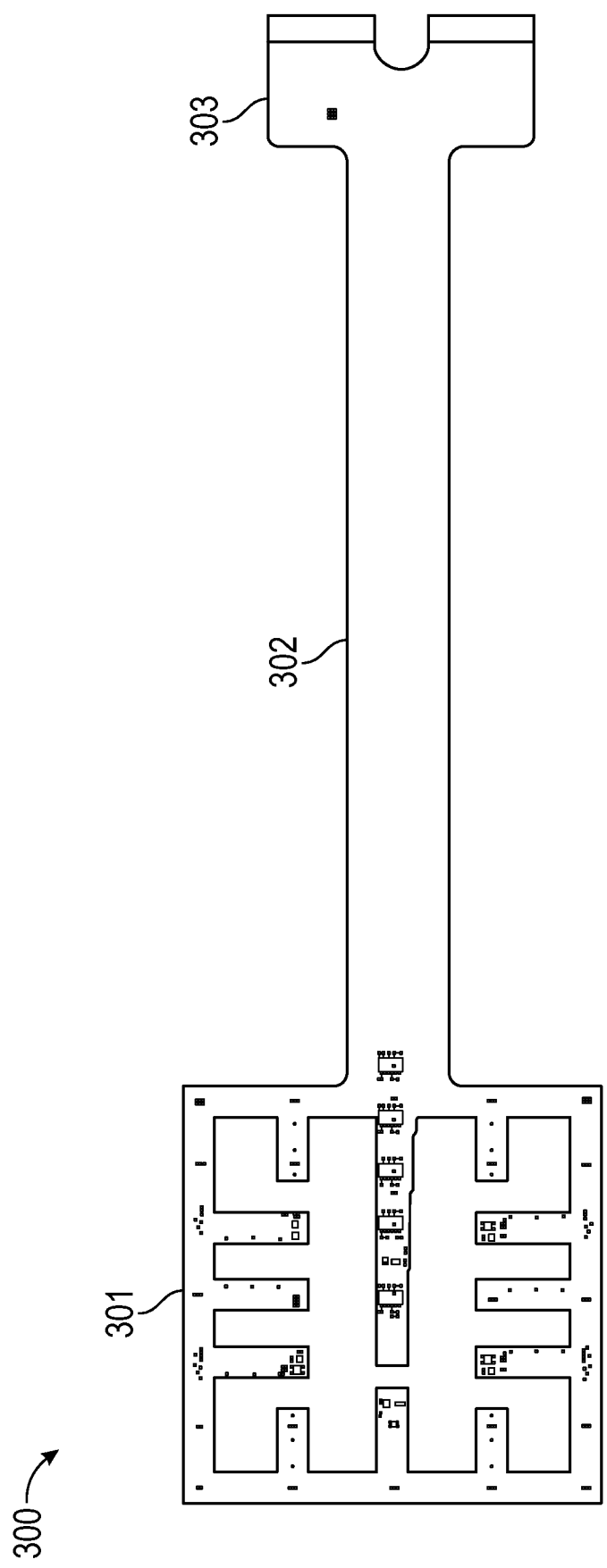
FIG. 3A illustrates a sensor array that may be incorporated into a wound dressing according to some embodiments.

FIG. 3A illustrates a sensor array 300 including a sensor portion 301, a tail portion 302, and a connector pad end portion 303. The sensor portion 301 can include one or more of a temperature sensor, impedance sensor, optical sensor, and SpO2 sensor, among other possible sensors, as well as associated circuitry. The sensor array 300 can be a flexible sensor array printed circuit. The tail portion 302 can extend from the sensor portion 301 to the connector pad end portion 303. The tail portion 302 can allow the control module to be placed distant from the wound, such as for example in a more convenient location away from the wound. The connector pad end portion 303 can electrically or electronically connect to a control module or other processing unit to receive the data from the sensor portion 301. The sensor array 300 can be incorporated onto or into a wound dressing like the wound dressing 200 of FIG. 2, such as in the wound contact layer 222 of the wound dressing 200.

Figure 3B:
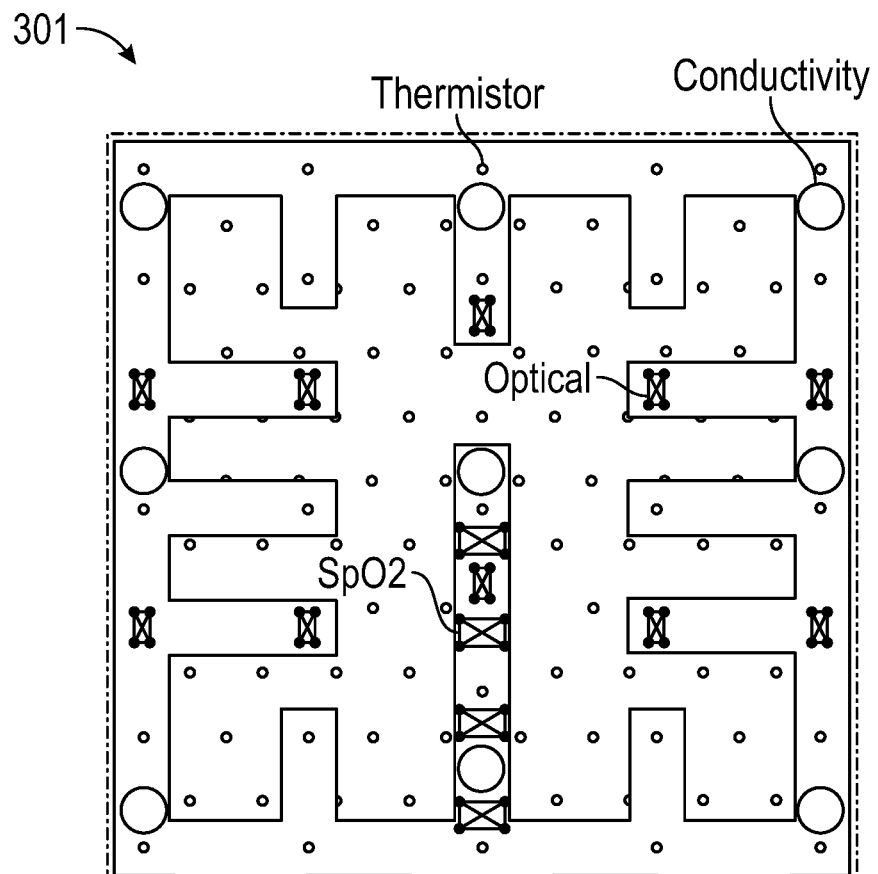
FIG. 3B illustrates a sensor portion of a sensor array according to some embodiments.

FIG. 3B illustrates the sensor portion 301 of the sensor array 300 of FIG. 3A according to some embodiments. The sensor portion 301 can include a plurality of portions that extend either around a perimeter of a wound dressing component such as a wound contact layer, or inward from an outer edge of the wound dressing component. For example, the embodiment illustrated in FIG. 3B includes a plurality of linearly extending portions that may be parallel to edges of a wound dressing component, and in some embodiments, follow the entire perimeter of the wound dressing component. In some embodiments, the sensor portion 301 may comprise a first plurality of parallel linearly extending portions that are perpendicular to a second plurality of parallel linearly extending portions. These linearly extending portions may also have different lengths and may extend inward to different locations within an interior of a wound dressing component. In some embodiments, the sensor portion 301 does not cover the entire wound dressing component, so that gaps are formed between portions of the sensor array 300.

As can be seen from FIG. 3B, one or more temperature sensors, impedance sensors (or conductivity sensors), SpO2 sensors, or optical, ultraviolet (UV), infrared (IR), or other type of visible or invisible light sensors can be used on the sensor array to provide information relating to conditions of the wound. Optical, ultraviolet (UV), infrared (IR), or other type of visible or invisible light or other electromagnetic spectrum sensors can provide spectral measurement(s) of the wound. The one or more sensors can assist a clinician in monitoring the healing of the wound and operate individually or in coordination with each other to provide data relating to the wound and wound healing characteristics.

An impedance sensor can be, for example, used to determine the difference between living and dead tissue or to show a change in impedance due to a wound being opened up in morbid tissue. The impedance sensors can include Ag/AgCl electrodes and an impedance analyzer. The impedance sensor can, for instance, be used to measure the change of impedance of a region of wound growth by measuring the impedance of the surrounding tissue/area. The impedance sensor can be used in the wound bed or on the perimeter of the wound or may be used to detect adherence failure of the dressing.

The sensor portion 301 can, in some implementations, utilize impedance sensors to measure the change in impedance on perimeter electrodes due to a wound size or wound shape change. For example, tomographic reconstruction or techniques can be used to infer wound size by using different spacing of impedance sensors or electrodes. Voltage or current probes can be used to apply voltage or current stimuli to determine or test patient's nerve responses or to promote wound healing. Impedance can be measured through a conductive path that goes through a biocompatible layer (for example, of the wound dressing) or through a biocompatible gel layer (for example, conductive gel layer) or saline solution to contact the wound. Measurements can be made in a frequency range of about 2.5 kHz to about 100 kHz. This can be similar to using large patch clamp measurements.

Alternatively or additionally, impedance can be measured using capacitance or a capacitive-coupling method without forming direct contact with the tissue (for example, using non-contact electrodes). For example, transmission in the frequency range of about 30 kHz to about 70 kHz can be used. Impedance can be measured using three point probe measurement or four point probe measurement. Impedance of one or more of wound tissue or exudate can be measured, which can be used to infer cell or tissue health. Impedance of a region around a wound (such as, skin or tissue surrounding the wound) can be measured. Impedance sensors can be retractable to move in out as needed. Impedance sensors can include fine or micro probe needles with conductive tips which extend into the wound and insulating shafts. The impedance sensor can be dangling probes under a wound contact layer, which come into contact with the wound. The impedance sensor can include dry contact electrodes. The impedance sensors can include electrodes, such as gold, silver, platinum, or carbon electrodes, that ensure or promote biocompatibility.

Temperature sensors can use thermocouples or thermistors to measure temperature. The thermistors can be used to measure or track the temperature of the underlying wound or the thermal environment within the wound dressing. The thermometry sensors can be calibrated and the data obtained from the sensors can be processed to provide information about the wound environment. An ambient sensor measuring ambient air temperature can also be used to assist in eliminating problems associated with environment temperature shifts.

Optical sensors can be used to measure wound appearance using an RGB sensor with an illumination source. In some embodiments, both the RGB sensor and the illumination source would be pressed up against the skin, such that light would penetrate into the tissue and take on the spectral features of the tissue itself.

Light propagation in tissue can be dominated by two major phenomena, scattering and attenuation. For attenuation, as light passes through tissue, its intensity may be lost due to absorption by various components of the tissue. Blue light tends to be attenuated heavily, whilst light at the red end of the spectrum tends to be attenuated least.

Scattering processes can be more complex, and can have various "regimes" which must be considered. The first aspect of scattering is based on the size of the scattering centre compared with the wavelength of incident light. If the scattering center is much smaller than the wavelength of light, then Rayleigh scattering can be assumed. If the scattering center is on the order of the wavelength of light, then a more detailed Mie scattering formulation must be considered. Another factor involved in scattering light is the distance between input and output of the scattering media. If the mean free path of the light (the distance between scattering events) is much larger than the distance travelled, then ballistic photon transport is assumed. In the case of tissue, scatting events are approximately 100 microns apart—so a 1 mm path distance would effectively randomize the photon direction and the system would enter a diffusive regime.

Ultra bright light emitting diodes (LEDs), an RGB sensor, and polyester optical filters can be used as components of the optical sensors to measure through tissue color differentiation. For example, because surface color can be measured from reflected light, a color can be measured from light which has passed through the tissue first for a given geometry. This can include color sensing from diffuse scattered light, from an LED in contact with the skin. In some embodiments, an LED can be used with an RGB sensor nearby to detect the light which has diffused through the tissue. The optical sensors can image with diffuse internal light or surface reflected light.

Additionally, the optical sensors can be used to measure autofluorescence. Autoflourescense is used because the tissue is absorbing light at one wavelength, and emitting at another. Additionally, dead tissue may not auto-fluoresce and so this could be a very strong indication as to if the tissue is healthy or not. Due to blue light (or even UV light) having such a short penetration depth, it may be very useful for example to have a UV light with a red sensitive photodiode nearby (or some other wavelength shifted band) to act as a binary test for healthy tissue, which would auto-fluoresce at a very particular wavelength.

In some embodiments, pH changing pads can be used as a pH sensor. A spectrometer and a broadband white light source can be used to measure the spectral response of the pH dye. The illumination and imaging can be provided on the surface of the wound dressing that is in contact with the wound and at the same side as the fluid application, the bottom surface. Alternatively, in some embodiments, the illumination and imaging source can be provided on the surface of the wound dressing opposite the bottom surface and away from fluid application or the top surface of the dressing.

In some embodiments, pulse oximetry SpO2 sensors can be used. To measure how oxygenated the blood is and the pulsatile blood flow can be observed. Pulse oximetry measurements work by taking a time resolved measurement of light absorption/transmission in tissue at two different optical wavelengths. When hemoglobin becomes oxygenated, its absorption spectrum changes with regards to non-oxygenated blood. By taking a measurement at two different wavelengths, one gains a ratio metric measure of how oxygenated the blood is.

The components in the sensor array can be connected through multiple connections. In some embodiments, the thermistors can be arranged in groups of five. Each thermistor is nominally 10 kΩ, and each group of five has a common ground. There are five groups of thermistors, giving a total of 30 connections. In some embodiments, there can be nine conductivity terminals. Each conductivity terminal requires one connection, giving a total of 9 connections. In some embodiments, there can be five SpO2 sensors. Each SpO2 sensor requires three connections, plus power and ground (these are covered separately), giving a total of 15 connections. In some embodiments, there can be 10 color sensors. Each color sensor comprises an RGB LED and an RGB photodiode. Each color sensor requires six connections, however five of these are common to every sensor, giving a total of 15 connections. Power and ground are considered separately. In some embodiments, there can be 5 pH sensors. The pH sensors can be a color-change discs, and can be sensed using the color sensors described above. Therefore, the pH sensors require no additional connections. There can be three power rails, and seven ground return signals, giving a total of 10 common connections. In some embodiments, the sensor array can include 25 thermistor (Murata NCP15WB473E03RC), 9 conductivity terminal, 5 SpO2 (ADPD144RI), 10 RGB LED (such as KPTF-1616RGBC-13), 10RGB Color Sensor, 10 FET, a printed circuit board (PCB), and an assembly.

In certain implementations, a controller (such as a microprocessor) can be mounted on the wound dressing and connected to the one or more sensors. Such a mounted controller can communicate with a control module over a connection, such as 3 or 4 wire connection (or less or more wires), to alleviate burdens associated with connecting to external component(s). For example, the tail portion 302 can include a 3 or 4 wire connection. In some implementations, the mounted controller can communicate wirelessly.

The controller or control module can be used to interface with the sensor array 300. The control module can contain a power source, such as batteries, and electronics to drive the sensors. The control module can also log data at appropriate intervals and allow data transfer to an external computing device, such as a personal computer (PC). The control module can be customized to have various features depending on the sensors used in the sensor array 300 and the data collected by the sensors. The control module can be comfortable enough and small enough to be worn continuously for several weeks and may be positioned near the wound dressing or on the wound dressing. In some embodiments, the control module can be positioned in a remote location from the wound dressing and accompanying sensor array 300. The control module can communicate with the sensor array 300 and wound dressing through electrical wires or through wireless communication whether positioned on the dressing, near the dressing, or remote from the wound dressing. The control module, in some implementations, can determine a characteristic of the wound from the data collected by the sensor array 300 and activate an alarm responsive to the characteristic, such as to indicate the dead tissue is detected.

The control module can include various requirements and combination of features including but not limited to the features listed in Table 1 below.

TABLE 1

OPTIONAL FEATURES FOR CONTROL MODULE 7 day operation from a single set of batteries
28 day local, non-volatile, storage capacity
Easy to charge, or to replace battery
Wireless link to PC/tablet (such as Bluetooth)
Wired link to PC (optional, micro-USB)
Drive electronics for temperature sensors (such as, thermistors)

TABLE 1-continued

OPTIONAL FEATURES FOR CONTROL MODULE

Figure 3C:
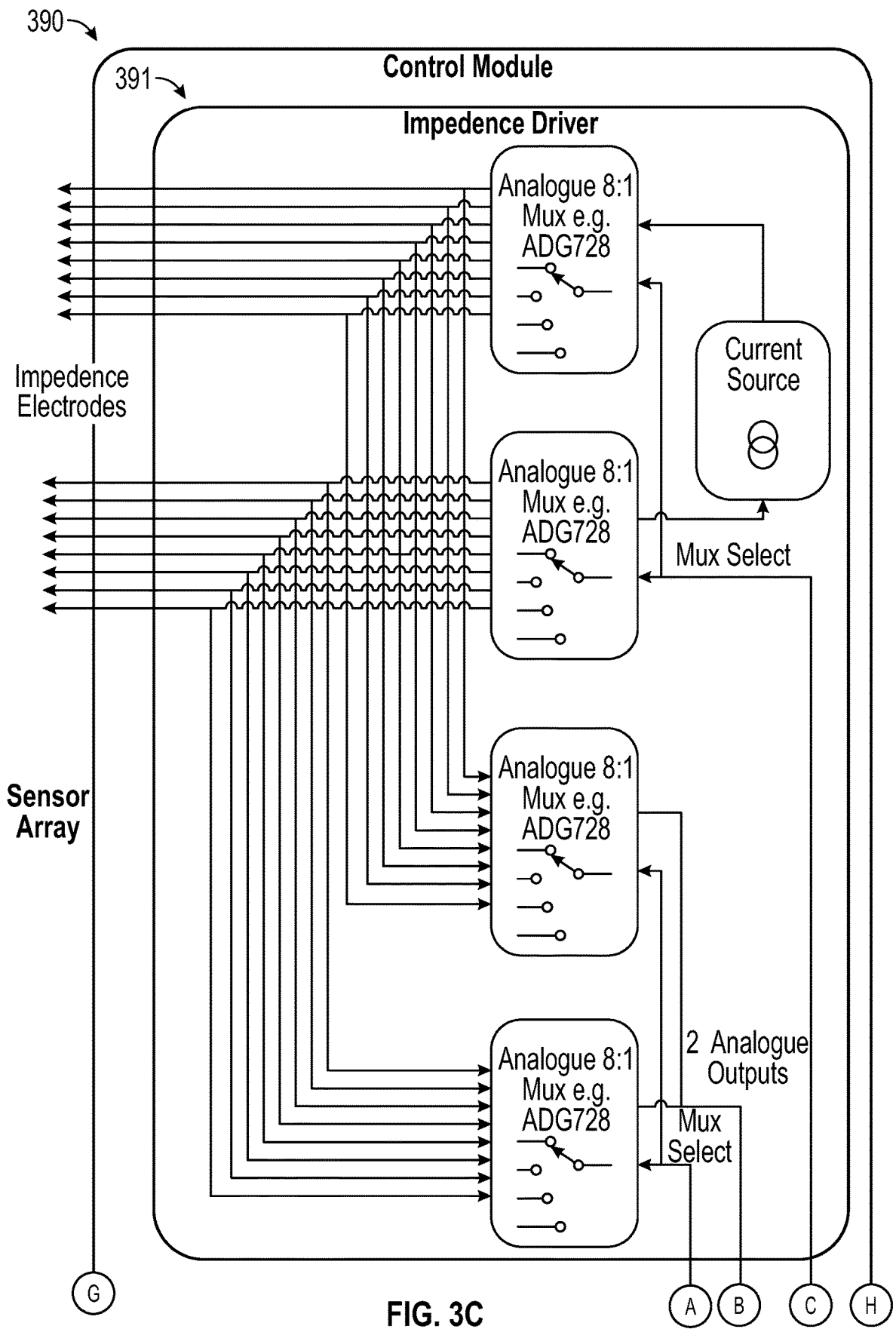
FIG. 3C illustrates a control module according to some embodiments.
Figure 3C:
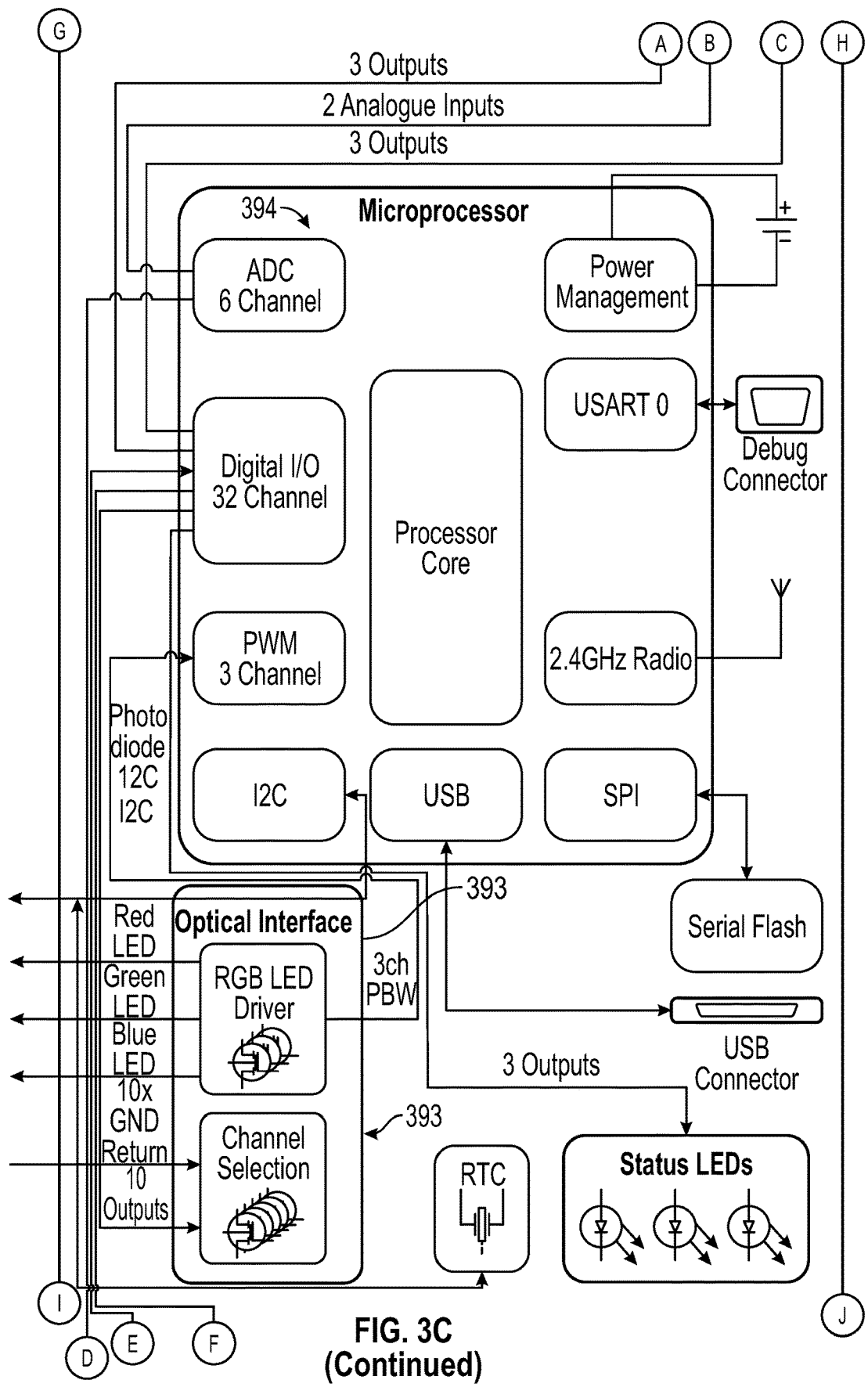
Figure 3C:
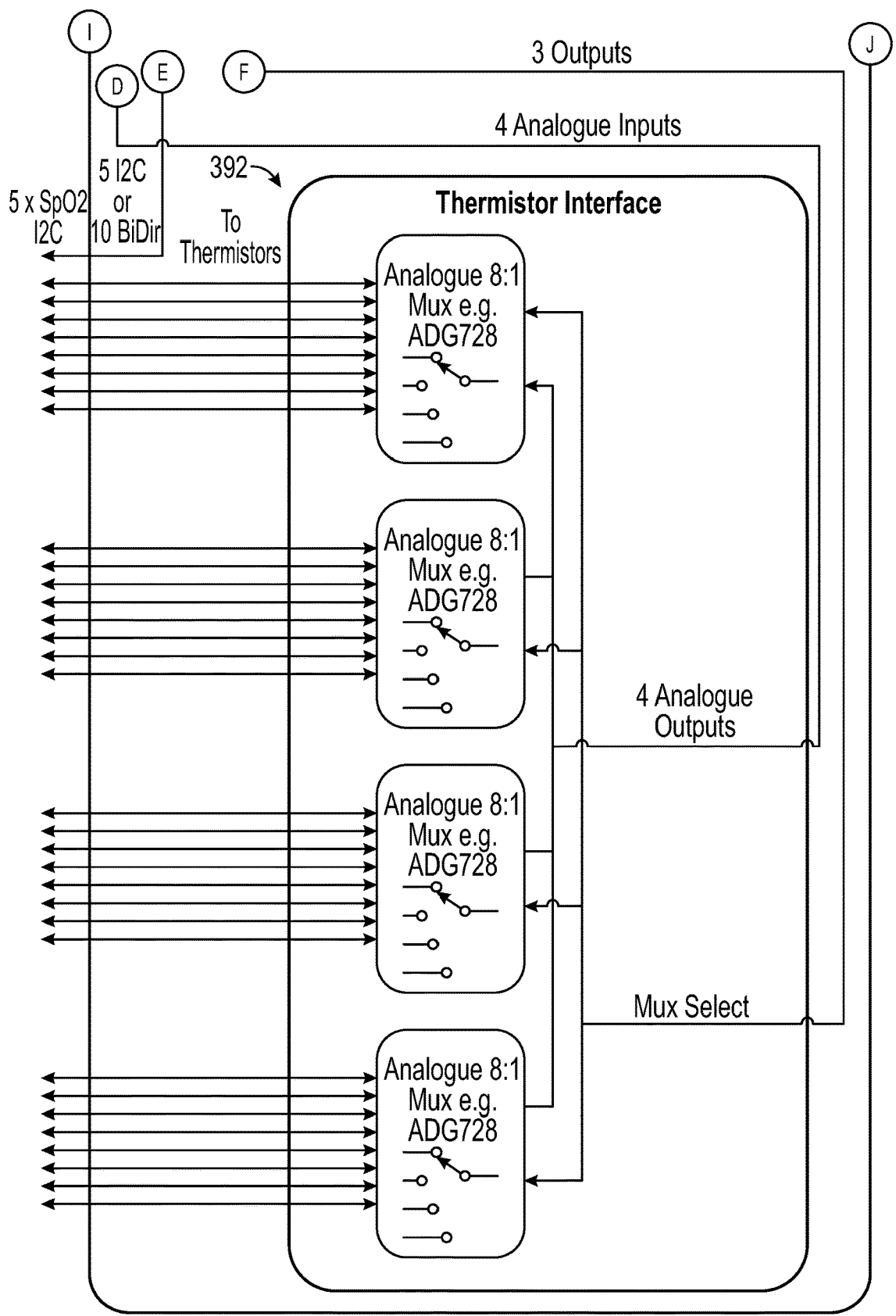

Drive electronics for impedance sensors
Drive electronics for optical sensors
Drive electronics for SpO2 sensors
Power management
Real Time Clock (RTC) to allow accurate data logging, and correlation with other measurands
Ability to change sample rates and intervals (useful for SpO2) for each sensor
Indication of status visually, audibly, tangibly, or the like. For example, via LED, such as (Green: Awake; Flashing green: Charging; Blue: Wireless link established; Flashing blue: Wireless data transfer; Yellow: Wired link established; Flashing yellow: Wired data transfer; Red: Battery low; Flashing red: Battery very low FIG. 3C illustrates a block diagram of a control module 390 according to some embodiments. The control module 390 includes an impedance driver box 391 supporting features of an impedance driver. Box 392 supports the features of the temperature sensor (for example, thermistor) interface, and box 393 supports the features of the optical interface. The control module 390 can include a controller or microprocessor 394 with features including a Real time clock (RTC), Status LEDs, USB connector, Serial Flash, and Debug Connector.

The microprocessor can have one or more of the following features: 2.4 GHz or another suitable frequency radio (either integrated, or external); Supplied Bluetooth software stack; SPI interface; USB (or UART for external USB driver); I2C; 3 channel PWM; 32 GPIO; or 6-channel ADC. In some embodiments, the device can require at least 48 I/O pins or possibly more due to banking limitations. Bluetooth stack typically requires ~20 kB on-board Flash, so a minimum of 32 kB can be required. In some embodiment, 64 kB can be required if complex data processing is considered. The processor core can be ARM Cortex M4 or a similar processor core. In some embodiments, the parts can include ST's STM32L433LC or STM32F302R8, which would require an external radio, or NXP's Kinetis KW range including integrated radio.

The control module can include a memory component where the amount of local storage depends on the sample rate and resolution of the sensors. The control module can utilize one or more analogue switches. The control module can incorporate a power source, such as a battery, or may instead utilize a power source separate from the control module. The control module can incorporate a real time clock (RTC). The PCB of the control module can be a 4-layer board, approximately 50 mm×20 mm, or 25 mm×40 mm The type of PCB used can be largely driven by connection requirements to sensor array.

The data collected through the sensor array can be passed through the control module and processed by a host software. The software may be executed on a processing device. The processing device can be a PC, tablet format computing device or a tablet, smartphone, or other computer capable of running host software (for example, a custom made computing device). The processing device executing the software can be in communication with the control module through electrical wires or through wireless communication.

Electronics, including one or more of sensors or control module, can be constructed to be compatible or safe for x-ray, MRI, or other type of scanning. Electronics can be constructed to be compatible or safe with external or implantable defibrillators. Electronics can include protection against radiofrequency interference (RFI) or electromagnetic interference (EMI). For example, one or more EMI shields can be used, which can be made out of ferrite, copper, or another material. Faraday cages, or the like.

In some embodiments, a source of negative pressure (such as a pump) and some or all other components of the TNP system, such as power source(s), sensor(s), connector(s), user interface component(s) (such as button(s), switch(es), speaker(s), screen(s), etc.) and the like, can be integral with the wound dressing. In some embodiments, the components can be integrated below, within, on top of, or adjacent to the backing layer. In some embodiments, the wound dressing can include a second cover layer or a second filter layer for positioning over the layers of the wound dressing and any of the integrated components. The second cover layer can be the upper most layer of the dressing or can be a separate envelope that enclosed the integrated components of the TNP system.

As used herein the upper layer, top layer, or layer above refers to a layer farthest from the surface of the skin or wound while the dressing is in use and positioned over the wound. Accordingly, the lower surface, lower layer, bottom layer, or layer below refers to the layer that is closest to the surface of the skin or wound while the dressing is in use and positioned over the wound.

Electrostatic Discharge Protection

Components, such as sensors, connections, or the like, can be mounted on a sensor array, such as the sensor array 300 of FIG. 3A. The sensor array with sensors can, in turn, be part of or coupled to a wound dressing that is positioned in or on a wound, skin, or both the wound and the skin of a patient. The sensor array with sensors can be used to generate signals indicative of physiological parameter of the wound, skin, or patient. Moreover, the sensor array with sensors can be constructed to improve the tolerance of sensor array to environmental conditions and desirably can operate electrically or mechanically properly or safely in various non-controlled environments like home healthcare, airborne, automobile, boats, train, metal detectors, active implantable device, and the like.

One or more of the features described herein can enable the sensory array with sensors to withstand high levels of ESD or be defibrillation-proof The sensor array with sensors can be configured to withstand high levels of ESD and in multiples steps, such as contact: ±2 kV, ±4 kV, ±6 kV, ±8 kV or higher, and air: ±2 kV, ±4 kV, ±6 kV, ±8 kV ±15 kV, ±30 kV or higher. In addition, the sensor array with sensors can, in some implementations, be defibrillation-proof (for instance, defibrillation-proof as an entire applied part), such as is defined under the IEC 60601-1 standard, another standard, or other industry-accepted criteria. The sensor array with sensors can, for example, continue normal operation when monophasic or biphasic defibrillation shock is applied to a patient that is wearing the sensor array. The sensors of the sensory array may not change performance or present false information under or after such conditions. Such a defibrillation-proof construction can be desirable because sensors can then survive an external defibrillation shock in case a patient using the sensor array goes into cardiac arrest. Moreover, the sensor array can be defibrillator-proof while retaining usability (for example, not having a metal case, which may, for instance, add too much weight to the device).

The sensor arrays with sensors, as described herein, can advantageously, in certain embodiments, be constructed using a process illustrated by FIGS. 4A-4H or one or more features of the process or variations thereof.

Figure 4A:
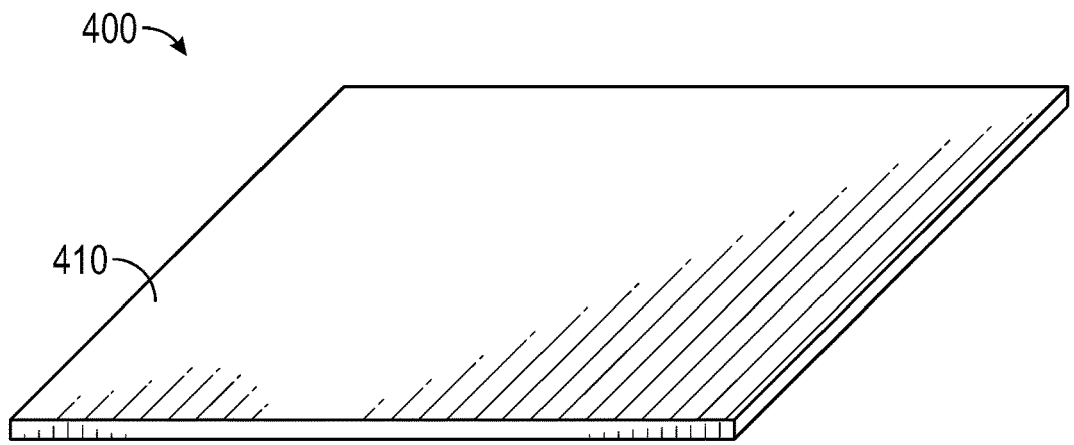

As illustrated in FIG. 4A, a process of constructing a circuit board 400 can begin with an elastomer substrate 410 being provided. The elastomer substrate 410 can be a stretchable or wound contact layer. The elastomer substrate 410 can, for instance, be composed of or include TPU. The elastomer substrate 410 can have a low permeability in some implementations.

Figure 4B:
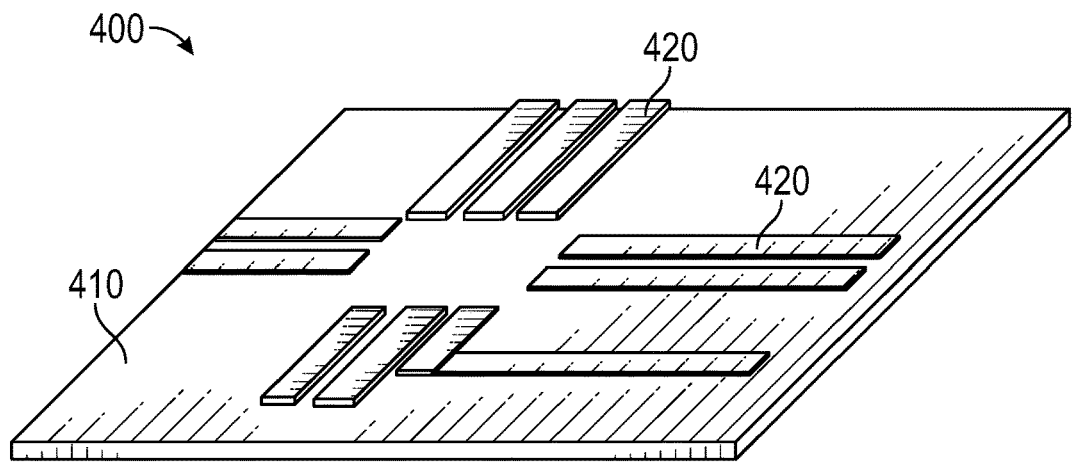
Figure 4C:
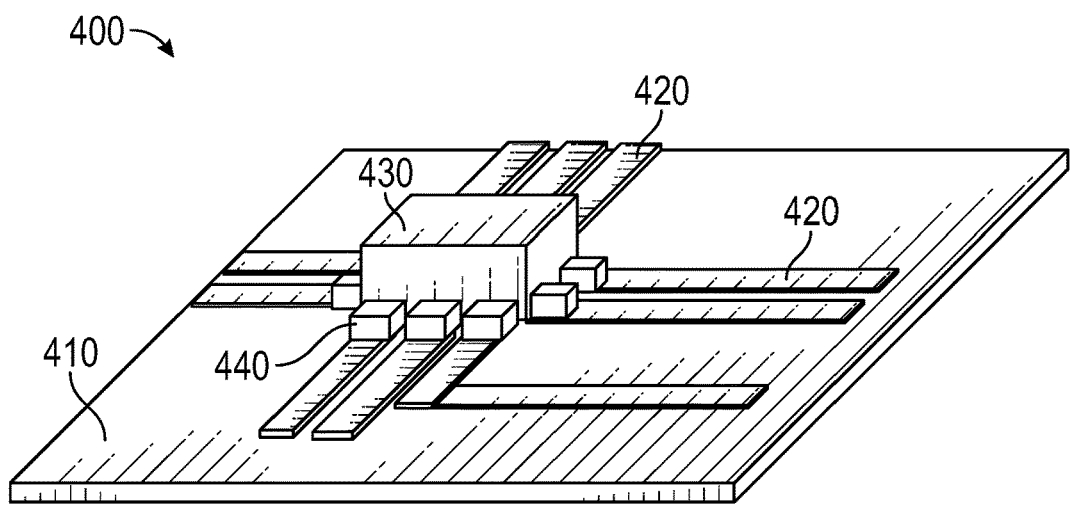

Next, at FIG. 4B, conductive tracks 420 can be placed on the elastomer substrate 410. For example, the conductive tracks 420 can be placed by printing ink tracks, such as copper-infused, silver-infused, silver-chloride, or gold-infused ink tracks. At FIG. 4C, one or more components 430 can be added to the elastomer substrate 410 and electrically connected with connectors 440 to the conductive tracks 420. The one or more components 430 can, for instance, include or be temperature sensors, impedance sensors (or conductivity sensors), SpO2 sensors, or optical, ultraviolet (UV), infrared (IR), or other type of visible or invisible light sensors, or the like. The connectors 440 can be pins, leads, bumps, or the like. At least some of the conductive tracks 420 or the connectors 440 can be flexible or stretchable or substantially flexible or stretchable.

Figure 4D:
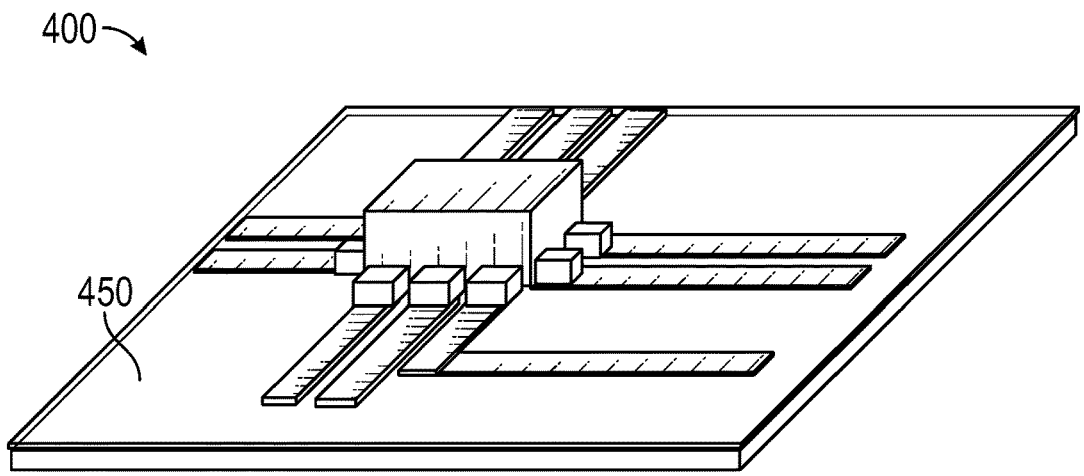

At FIG. 4D, a conformal coating 450 can be applied to a component side of the elastomer substrate 410. The conformal coating 450 can be used to encapsulate one or more of the elastomer substrate 410 or items supported on the coated side of the elastomer substrate 410. The conformal coating 450 can, for example, be applied with a spray, brush, or another approach and cured using one or more of UV, light, or thermal curing. The conformal coating 450 can one or more of a suitable polymer, adhesive, such as 1072-M UV, light, or thermal curable or cured adhesive, Optimax adhesive (such as, NovaChem Optimax 8002-LV), parylene (such as, Parylene C), silicon, epoxy, urethane, acrylated urethane, or another suitable biocompatible and stretchable material. The conformal coating 450 can be thin, such as about 100 microns thick, less than about 100 microns thick, or more than about 100 microns thick.

Figure 4E:
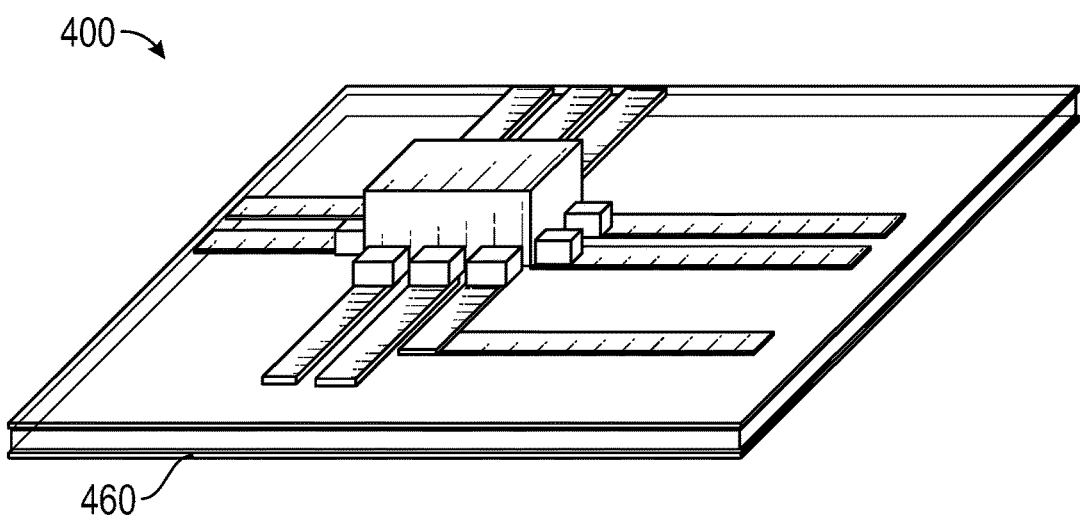

At FIG. 4E, a conformal coating 460 can be applied to a non-component side of the elastomer substrate 410. The conformal coating 460 can be used to encapsulate one or more of the elastomer substrate 410 or items supported on the coated side of the elastomer substrate 410. The conformal coating 460 can, for example, be applied with a spray, brush, or another approach and cured using one or more of UV, light, or thermal curing. The conformal coating 460 may be the same type or a different type of coating than the conformal coating 450.

Figure 4F:
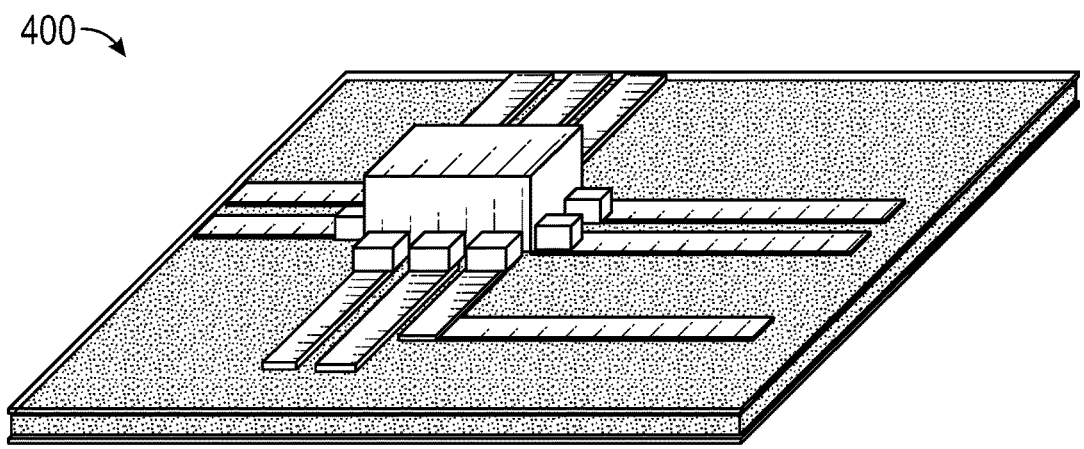

At FIG. 4F, the circuit board 400 can be perforated. For example, at least the elastomer substrate 410 can be perforated using one or more of a cold pin perforation, hot pin perforation, laser ablation perforation, ultrasonic or ultrasound perforation, or the like to make the elastomer substrate 410 permeable to liquid or gas.

At FIG. 4G, a top edge plane 470 and a through vias 480 can be added to the elastomer substrate 410. The top edge plane 470 and the through vias 480 can be added, for example, by printing ink tracks or dipping or overmolding tracks onto the elastomer substrate 410. The top edge plane 470 can be a conductive pathway extending around all or part (for instance, 20%, 25%, 30%, 35%, 40%, 45%, 50%, 55%, 60%, 65%, 70%, 75%, 80%, 85%, 90%, or 95% of a length) of a perimeter or an edge of one side of the elastomer substrate 410 or at least a portion of the elastomer substrate 410 on which one or more sensors are positioned.

The top edge plane 470 and the through vias 480 can be connected to electrical ground of the elastomer substrate 410 and the one or more components 430 (for instance, to a negative voltage of a power supply) and serve to protect the one or more components 430 when the elastomer substrate 410 is exposed to ESD by providing a discharge path for the ESD. The through vias 480 can include multiple vias that are conductive pathways through the elastomer substrate 410 and electrically connect the top edge plane 470 to a surface on an opposite side of the elastomer substrate 410 through the elastomer substrate 410. The conductive pathways of the through vias 480 can partially or fully fill the vias. The through vias 480 can be spaced apart from one another between around 1 mm to 10 mm, such as around 2.5 mm, but can be spaced apart a lesser or greater spacing in some implementations.

At FIG. 4H, a bottom edge plane 490 can be added to the elastomer substrate 410. The bottom edge plane 490 can be added, for example, by printing ink tracks or dipping or overmolding tracks onto an opposite side of the elastomer substrate from the top edge plane 470. The bottom edge plane 490 can be a conductive pathway extending around all or part (for instance, 20%, 25%, 30%, 35%, 40%, 45%, 50%, 55%, 60%, 65%, 70%, 75%, 80%, 85%, 90%, or 95% of a length) of a perimeter or an edge of the elastomer substrate 410 or at least a portion of the elastomer substrate 410 on which one or more sensors are positioned. The bottom edge plane 490 can be electrically connected to the conductive pathways of the through vias 480 and thus electrical ground and further serve to protect the one or more components when the elastomer substrate 410 is exposed to ESD by providing a discharge path for the ESD.

Upon completion of the process illustrated by FIGS. 4A-4H, the one or more components 430 can communicate with a control module, such as the control module 390 of FIG. 3C, via the conductive tracks 420. The control module can, in turn, monitor or adjust operations of the one or more components 430 through the communications.

The process described with respect to FIGS. 4A-4H H can be varied in one or more of the following ways: A conformal coating may not be applied to the non-component side of the elastomer substrate 410 as shown at FIG. 4E. A conformal coating may be applied to the non-component side of the elastomer substrate 410 prior to placing the conductive tracks 420 on the elastomer substrate 410 rather than after. The top edge plane 470 and the bottom edge plane 490 can be placed prior to perforation and then back-filled. The top edge plane 470 and the bottom edge plane 490 can be linked around an outside of the elastomer substrate 410 rather than by the through vias 480. Edge immunity can be achieved by using a material on the non-component side overlapping and an overhang can be adhered to the underside, and protection may then be provided using a conductive material (for example, metalized polyethylene film) or an insulating material (for example, PVC film). The film can additionally or alternatively be positioned on both sides, overlapping and perforated through, welding both the edge and perforations.

Figure 5:
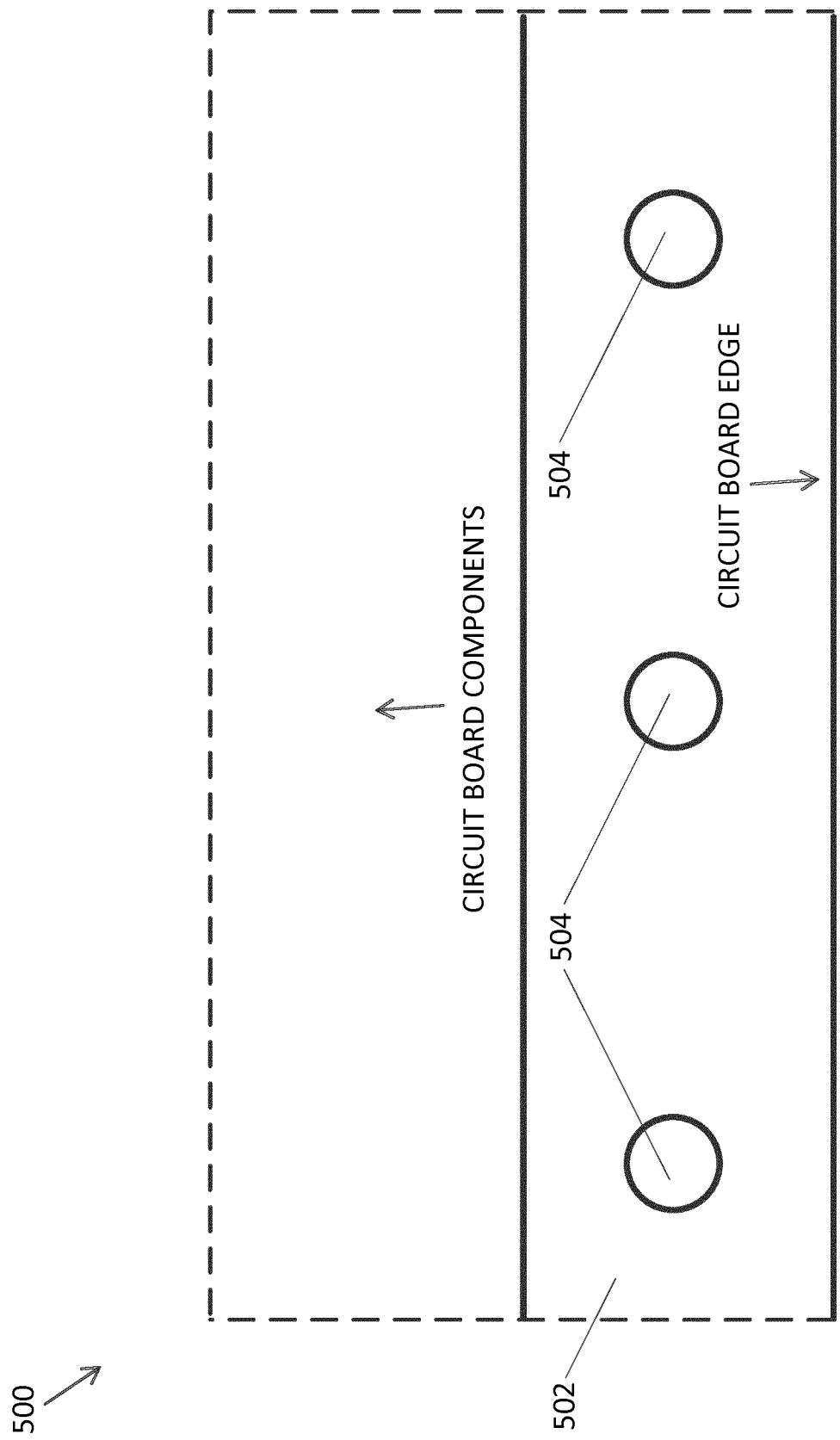
FIG. 5 illustrates a top view of an edge area of a circuit board according to some embodiments.

FIG. 5 illustrates a top view of an edge area 500 of a circuit board, such as the circuit board 400 of FIG. 4G, that includes a top ground plane 502 and through vias 504. The top ground plane 502 can include a conductive pathway positioned proximate to a circuit board edge, such as an outer edge of the circuit board or an inner edge of the circuit board. The conductive pathway can separate the circuit board edge from circuit board components mounted on the circuit board and may or may not be positioned against the circuit board edge.

The through vias 504 can be holes in the conductive pathway.

Figure 6A:
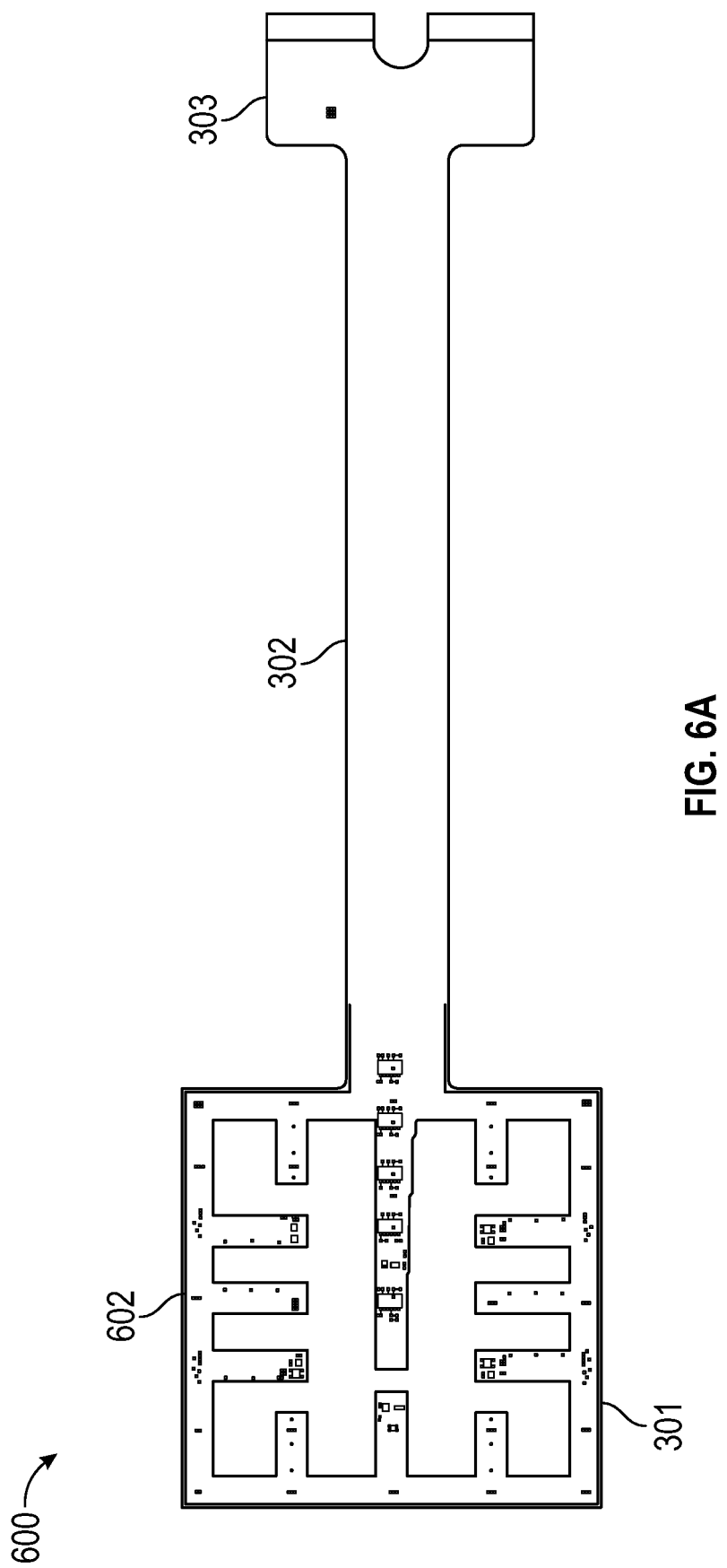
FIGS. 6A-6C illustrate sensor arrays that include edge planes for protecting against electrostatic discharge according to some embodiments.

FIG. 6A illustrates a sensor array 600 that may be the same as the sensor array 300 of FIG. 3A except that a top edge plane 602 is shown extending around a perimeter of the sensor portion 301. The top edge plane 602 can be like the top edge plane 470 and provide ESD protection to one or more sensors or associated circuitry mounted to the sensor portion 301 or the tail portion 302. For example, the top edge plane 602 can protect one or more of a temperature sensor, impedance sensor, optical sensor, and SpO2 sensor mounted on the sensor portion 301 from an electrical current received by the sensor array 600 from external to the sensor array 600. Through vias, as described herein, may or may not be included in the top edge plane 602.

Figure 6B:
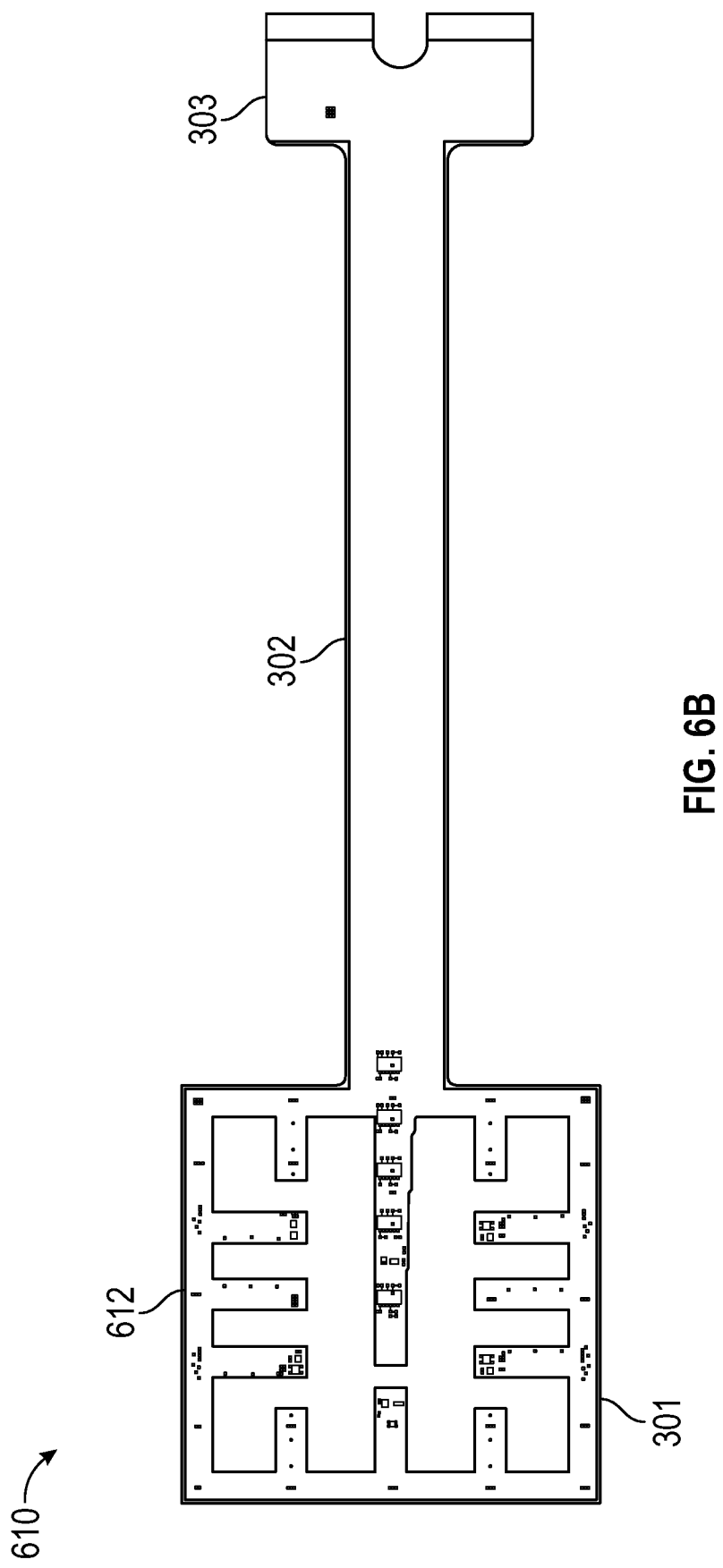

FIG. 6B illustrates a sensor array 610 that may be the same as the sensor array 600 of FIG. 6A except that a top edge plane 612 may extend farther along the tail portion and the connector pad end portion 303 than the top edge plane 602.

Figure 6C:
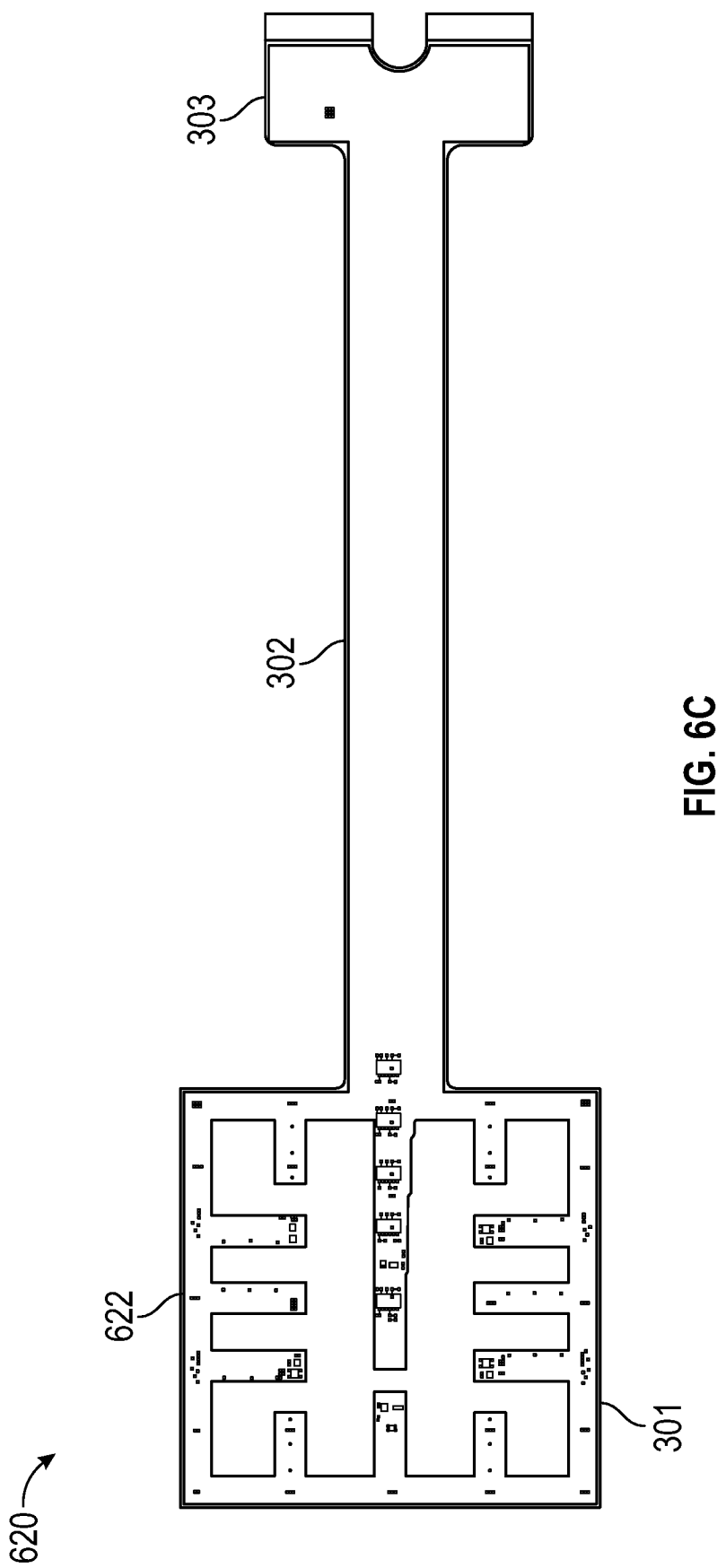

FIG. 6C illustrates a sensor array 620 that may be the same as the sensor array 610 of FIG. 6B except that a top edge plane 622 may extend farther along the connector pad end portion 303 than the top edge plane 612 and form a fully-connected loop.

Although FIGS. 6A-6C illustrate top edge planes extending around a part or all of an outer perimeter of the sensor portion 301, the tail portion 302, and the connector pad end portion 303, the top edge planes can be positioned differently on the sensor portion 301, the tail portion 302, and the connector pad end portion 303 or yet other edge planes can be positioned on the sensor portion 301, the tail portion 302, and the connector pad end portion 303. For example, an edge plane can extend around an inner perimeter of the sensor portion 301 rather than or in addition to an outer perimeter of the sensor portion 301. As another example, an edge plane can extend individually or in groups around one or more of the sensors or other components mounted on the sensor array.

Moreover, although not illustrated, bottom edge planes may be included on an opposite side of the sensor portion 301, the tail portion 302, and the connector pad end portion 303 from the top edge planes illustrated in FIGS. 6A-6C. The bottom edge planes can accordingly be electrically connected to the top edge planes by through vias.

Figure 7:
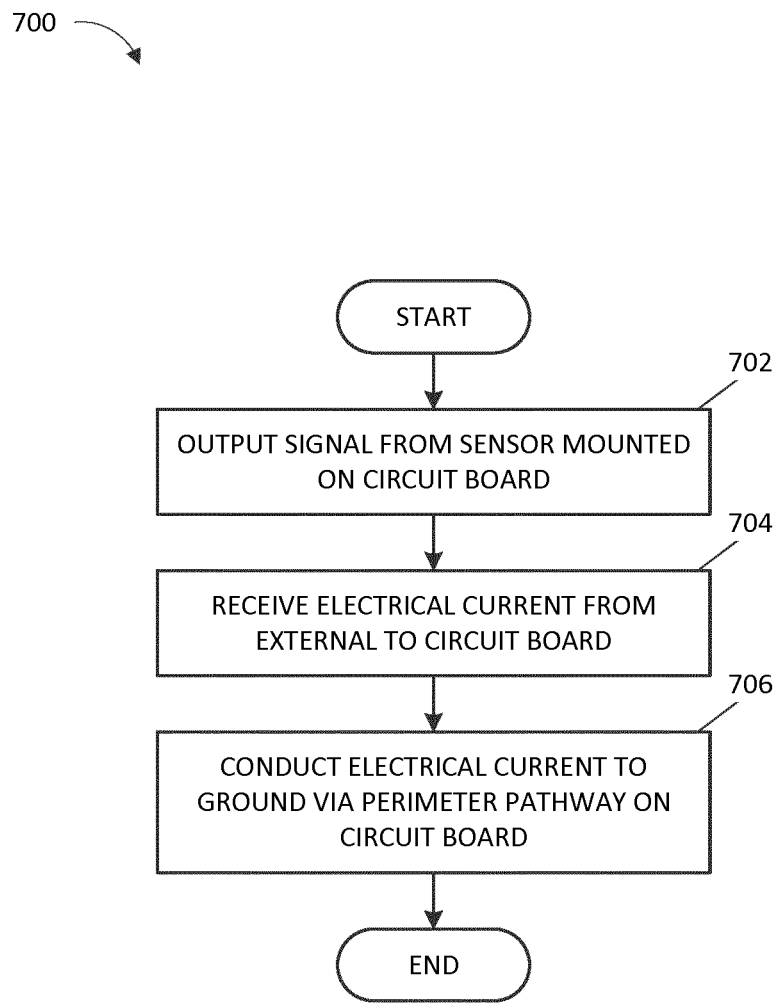
FIG. 7 illustrates a method for protecting a sensor from electrical discharge according to some embodiments.

FIG. 7 illustrates a method 700 for protecting a sensor from electrical discharge. The method 700 can be performed by a circuit board that supports a sensor, such as the circuit board 400 of FIG. 4H, the sensor array 600 of FIG. 6A, the sensor array 610 of FIG. 6B, the sensor array 620 of FIG. 6C. For convenience, the method 700 is explained in the context of the circuit boards described herein, but may instead be implemented in other systems not shown. The method 700 can advantageously, in certain embodiments, enable a sensor to be protected from electrical discharge that would traditionally have damaged the sensor. Moreover, the method 700 can provide enhanced protection for a sensor that may be positioned by a sensitive area, such as near a wound or proximate pressure therapy, where troubleshooting or fixing any issues with the sensor may be difficult or even impossible.

At block 702, the method 700 can output a signal from a sensor mounted on a circuit board. For example, a sensor mounted on the tail portion 301 of the sensor array 600 can output a signal responsive to and usable to determine a value indicative of a physiological parameter. The circuit board can be part of or coupled to a wound dressing.

At block 704, the method 700 can receive an electrical current from external to the circuit board. For example, the sensor array 600 can receive an electrical discharge from external to the wound dressing, such as from a defibrillation shock to a wearer of the wound dressing that passes to the sensor array 600.

At block 706, the method 700 can conduct the electrical current to ground via a perimeter pathway on the circuit board. The perimeter pathway can be a conductive pathway electrically coupled to ground for the circuit board and that extends around all or part (for instance, 20%, 25%, 30%, 35%, 40%, 45%, 50%, 55%, 60%, 65%, 70%, 75%, 80%, 85%, 90%, or 95% of a length) of an inner or outer perimeter of a side of the circuit board or a perimeter of one or more elements on or holes in the circuit board. The perimeter pathway can desirably be used to dissipate the electrical current without damaging the one or more sensors or associated circuitry be mounted on the circuit board. One example of the perimeter pathway is the top edge plane 602.

Other Variations

Any value of a threshold, limit, duration, etc. provided herein is not intended to be absolute and, thereby, can be approximate. In addition, any threshold, limit, duration, etc. provided herein can be fixed or varied either automatically or by a user. Furthermore, as is used herein relative terminology such as exceeds, greater than, less than, etc. in relation to a reference value is intended to also encompass being equal to the reference value. For example, exceeding a reference value that is positive can encompass being equal to or greater than the reference value. In addition, as is used herein relative terminology such as exceeds, greater than, less than, etc. in relation to a reference value is intended to also encompass an inverse of the disclosed relationship, such as below, less than, greater than, etc. in relations to the reference value. Moreover, although blocks of the various processes may be described in terms of determining whether a value meets or does not meet a particular threshold, the blocks can be similarly understood, for example, in terms of a value (i) being below or above a threshold or (ii) satisfying or not satisfying a threshold.

Features, materials, characteristics, or groups described in conjunction with a particular aspect, embodiment, or example are to be understood to be applicable to any other aspect, embodiment or example described herein unless incompatible therewith. All of the features disclosed in this specification (including any accompanying claims, abstract and drawings), or all of the steps of any method or process so disclosed, may be combined in any combination, except combinations where at least some of such features or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described herein may be embodied in a variety of other forms. Furthermore, various omissions, substitutions and changes in the form of the methods and systems described herein may be made. Those skilled in the art will appreciate that in some embodiments, the actual steps taken in the processes illustrated or disclosed may differ from those shown in the figures. Depending on the embodiment, certain of the steps described above may be removed, others may be added. For example, the actual steps or order of steps taken in the disclosed processes may differ from those shown in the figure. Depending on the embodiment, certain of the steps described above may be removed, others may be added. For instance, the various components illustrated in the figures may be implemented as software or firmware on a processor, controller, ASIC, FPGA, or dedicated hardware. Hardware components, such as controllers, processors, ASICs, FPGAs, and the like, can include logic circuitry. Furthermore, the features and attributes of the specific embodiments disclosed above may be combined in different ways to form additional embodiments, all of which fall within the scope of the present disclosure.

Conditional language, such as "can," "could," "might," or "may," unless specifically stated otherwise, or otherwise understood within the context as used, is generally intended to convey that certain embodiments include, while other embodiments do not include, certain features, elements, or steps. Thus, such conditional language is not generally intended to imply that features, elements, or steps are in any way required for one or more embodiments or that one or more embodiments necessarily include logic for deciding, with or without user input or prompting, whether these features, elements, or steps are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

All of the features disclosed in this specification (including any accompanying exhibits, claims, abstract and drawings), or all of the steps of any method or process so disclosed, may be combined in any combination, except combinations where at least some of such features or steps are mutually exclusive. The disclosure is not restricted to the details of any foregoing embodiments. The disclosure extends to any novel one, or any novel combination, of the features disclosed in this specification (including any accompanying claims, abstract and drawings), or to any novel one, or any novel combination, of the steps of any method or process so disclosed.

Various modifications to the implementations described in this disclosure may be readily apparent to those skilled in the art, and the generic principles defined herein may be applied to other implementations without departing from the spirit or scope of this disclosure. Thus, the disclosure is not intended to be limited to the implementations shown herein, but is to be accorded the widest scope consistent with the principles and features disclosed herein.

What is claimed:

1. An apparatus for use in monitoring or treating a wound, the apparatus comprising:
 a wound dressing configured to be positioned over a wound of a patient and absorb wound exudate from the wound, the wound dressing comprising a wound contact layer and an absorbent layer, the wound contact layer having a surface area that is at least as large as the absorbent layer and configured to contact the wound, the wound contact layer being flexible, the absorbent layer being configured to store the wound exudate;
 an elastomer substrate incorporated in or coupled to the wound contact layer, the elastomer substrate being flexible and having a first conductive pathway formed from ink on at least part of a perimeter of a first side of the elastomer substrate, the first conductive pathway being electrically coupled to an electrical ground plane for the elastomer substrate, the electrical ground plane being formed from ink;
 a sensor mounted on the elastomer substrate, the sensor being configured to output a signal usable to determine a value indicative of a physiological parameter of the patient; and
 a conformal coating comprising biocompatible material and encapsulating the elastomer substrate and the sensor,
 wherein the first conductive pathway is configured to protect the sensor against an electrostatic discharge.

2. The apparatus of claim 1, wherein the elastomer substrate is incorporated in the wound contact layer.

3. The apparatus of claim 1, wherein the elastomer substrate is stretchable.

4. The apparatus of claim 1, wherein the elastomer substrate comprises a second conductive pathway formed from ink on at least part of a perimeter of a second side of the elastomer substrate opposite the first side, the second conductive pathway being electrically coupled to the electrical ground plane and configured to protect the sensor against the electrostatic discharge.

5. The apparatus of claim 4, further comprising a plurality of vias electrically connecting the first conductive pathway and the second conductive pathway through the elastomer substrate.

6. The apparatus of claim 1, wherein the first conductive pathway extends around at least half of the perimeter of the first side.

7. The apparatus of claim 1, wherein the sensor is configured to continue to output the signal subsequent to the wound dressing being exposed to a defibrillation shock.

8. The apparatus of claim 1, wherein the sensor comprises one or more of a temperature sensor, an impedance sensor, an optical sensor, or a SpO2 sensor.

9. The apparatus of claim 1, further comprising a controller configured to receive the signal, determine the value, and output the value for presentation.

10. The apparatus of claim 9, wherein the controller is not mounted on the elastomer substrate.

11. The apparatus of claim 1, wherein the wound contact layer is perforated to transport the wound exudate to the absorbent layer.

12. The apparatus of claim 11, wherein the elastomer substrate is perforated.

13. A method for manufacturing an apparatus for use in monitoring or treating a wound, the method comprising:
 mounting a sensor on an elastomer substrate and in electrical communication with conductive tracks on the elastomer substrate, the elastomer substrate being flexible;
 forming a first conductive pathway from ink on at least part of a perimeter of a first side of the elastomer substrate;
 electrically connecting the first conductive pathway to an electrical ground plane for the elastomer substrate;
 applying a conformal coating to the elastomer substrate, the conformal coating comprising biocompatible material and encapsulating the elastomer substrate and the sensor; and
 incorporating the elastomer substrate into a wound contact layer of a wound dressing or coupling the elastomer substrate to the wound contact layer, the wound dressing comprising the wound contact layer and an absorbent layer, the wound contact layer having a surface area that is at least as large as the absorbent layer and configured to contact the wound, the wound contact layer being flexible, the absorbent layer being configured to store wound exudate.

14. The method of claim 13, wherein the elastomer substrate is stretchable.

15. The method of claim 13, wherein the elastomer substrate comprises thermoplastic polyurethane.

16. The method of claim 13, wherein said forming comprises forming the first conductive pathway so that the first conductive pathway extends around at least half of the perimeter of the first side.

17. The method of claim 13, further comprising:
 forming a second conductive pathway from ink on at least part of a perimeter of a second side of the elastomer substrate opposite the first side; and
 electrically connecting the second conductive pathway to the electrical ground plane.

18. The method of claim 17, further comprising electrically connecting the first conductive pathway to the second conductive pathway through the elastomer substrate.

19. The method of claim 17, further comprising electrically connecting the first conductive pathway to the second conductive pathway around an edge of the elastomer substrate.

* * * * *